(12) United States Patent
Makeiff et al.

(10) Patent No.: US 8,703,988 B2
(45) Date of Patent: *Apr. 22, 2014

(54) SELF-ASSEMBLED NANOSTRUCTURES

(75) Inventors: Darren Andrew Makeiff, St. Albert (CA); Rina Carlini, Oakville (CA)

(73) Assignees: Xerox Corporation, Norwalk, CT (US); National Research Council of Canada, Ottawa (CA)

( * ) Notice: Subject to any disclaimer, the term of this patent is extended or adjusted under 35 U.S.C. 154(b) by 37 days.

This patent is subject to a terminal disclaimer.

(21) Appl. No.: 12/820,497

(22) Filed: Jun. 22, 2010

(65) Prior Publication Data
US 2011/0311813 A1 Dec. 22, 2011

(51) Int. Cl.
C07C 69/76 (2006.01)
C07C 229/00 (2006.01)
D02G 3/00 (2006.01)
B82Y 30/00 (2011.01)

(52) U.S. Cl.
USPC ............ 560/8; 562/458; 428/401; 977/762

(58) Field of Classification Search
None
See application file for complete search history.

(56) References Cited

U.S. PATENT DOCUMENTS

| | | | |
|---|---|---|---|
| 4,073,775 A | 2/1978 | Matsuo et al. |
| 4,138,568 A | 2/1979 | Hari et al. |
| 5,278,020 A | 1/1994 | Grushkin et al. |
| 5,290,654 A | 3/1994 | Sacripante et al. |
| 5,308,734 A | 5/1994 | Sacripante et al. |
| 5,344,738 A | 9/1994 | Kmiecik-Lawrynowicz et al. |
| 5,346,797 A | 9/1994 | Kmiecik-Lawrynowicz et al. |
| 5,364,729 A | 11/1994 | Kmiecik-Lawrynowicz et al. |
| 5,370,963 A | 12/1994 | Patel et al. |
| 5,403,693 A | 4/1995 | Patel et al. |
| 5,418,108 A | 5/1995 | Kmiecik-Lawrynowicz et al. |
| 5,679,138 A | 10/1997 | Bishop et al. |
| 6,706,864 B1 | 3/2004 | Vincent et al. |
| 7,160,380 B2 | 1/2007 | Maeta et al. |
| 7,312,011 B2 | 12/2007 | Patel et al. |
| 7,335,453 B2 | 2/2008 | Sacripante et al. |
| 7,358,022 B2 | 4/2008 | Farrugia et al. |
| 7,371,870 B2 | 5/2008 | Hosaka et al. |
| 7,402,371 B2 | 7/2008 | Sacripante et al. |
| 7,419,753 B2 | 9/2008 | Vanbesien et al. |
| 7,425,398 B2 | 9/2008 | Nosella et al. |
| 7,429,443 B2 | 9/2008 | Patel |
| 7,442,740 B2 | 10/2008 | Patel et al. |
| 7,503,973 B1 | 3/2009 | Carlini |
| 7,524,599 B2 | 4/2009 | Vanbesien et al. |
| 7,547,499 B2 | 6/2009 | Veregin et al. |
| 7,857,901 B2 | 12/2010 | Carlini et al. |
| 7,883,574 B2 | 2/2011 | Carlini et al. |
| 7,905,954 B2 | 3/2011 | Carlini et al. |
| 7,938,903 B2 | 5/2011 | Carlini et al. |
| 7,985,290 B2 | 7/2011 | Carlini et al. |
| 8,025,723 B2 | 9/2011 | Carlini et al. |
| 2005/0048121 A1 | 3/2005 | East et al. |
| 2005/0109240 A1 | 5/2005 | Maeta et al. |
| 2005/0176726 A1 | 8/2005 | Wang et al. |
| 2006/0063873 A1 | 3/2006 | Lin et al. |
| 2006/0084732 A1 | 4/2006 | Shakely et al. |
| 2007/0012221 A1 | 1/2007 | Maeta et al. |
| 2008/0306193 A1 | 12/2008 | Allen et al. |

FOREIGN PATENT DOCUMENTS

| | | |
|---|---|---|
| JP | A-2003-081948 | 3/2003 |
| JP | A-2003-082256 | 3/2003 |
| JP | A-2003-096056 | 4/2003 |
| JP | A-2003-252864 | 9/2003 |
| JP | A 2009-221266 | 10/2009 |
| WO | WO 2006/005536 | 1/2006 |
| WO | WO 2006/132443 | 12/2006 |

OTHER PUBLICATIONS

Schulz et al. (Reactive & Functional Polymers (1996), 30(1-3), 353-360).*
Cuppen et al. (Crystal Growth & Design, 2004, 4 (5), 989).*
Winn et al. (AIChE journal, 1998, 44 (11) 2501).*
Taulelle et al. (Chem. Eng. Technol., 2006, 29 (2), 239).*
Lee et al. (Chemical Physics Letters, 1999, 307, 327).*
http://www.dur.ac.uk/crystallography.group/imagesgroup/GrowCrystals.pdf.*
E. Cole et al., "Oxidations with Lead Tetraacetate. Oxidations of Benzimidazoles, Benzoxazoles, and Benzothiazoles," *Australian J. Chem.*, 1986, vol. 39, pp. 295-301.

(Continued)

*Primary Examiner* — Paul A Zucker
*Assistant Examiner* — Jennifer C Sawyer
(74) *Attorney, Agent, or Firm* — Oliff PLC

(57) ABSTRACT

Nanostructures are formed from alkylated derivatives of aromatic acids of the formula:

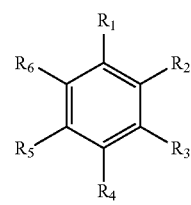

wherein at least one of $R_1$ to $R_6$ represents a carboxylic acid group, a primary amide group, an ester group, an amidine group, or a salt thereof, at least one other of $R_1$ to $R_6$ is $X-R_c$, and the remaining of $R_1$ to $R_6$ independently represent H or substituted or unsubstituted organic groups; X represents a linking group; and $R_c$ represents a substituted or unsubstituted alkyl group.

12 Claims, 7 Drawing Sheets

(56) References Cited

OTHER PUBLICATIONS

K. Balakrishnan et al., "Effect of Side-Chain Substituents on Self-Assembly of Perylene Diimide Molecules: Morphology Control," *J. Am. Chem. Soc.*, vol. 128, pp. 7390-98 (2006).
K. Hunger et al., "Uber die Molekul- und Kristallstruktur gelber Mono-"azo"-Pigmente," *Farbe + Lack*, vol. 88, pp. 453-458 (1982).
R. Clark et al., "Synthesis of Some Substituted Benzimidazolones," *J. Am. Chem. Soc.*, Apr. 5, 1958, vol. 80, pp. 1657-1662.
Hideki Maeta et al., "New Synthetic Method of Organic Pigment Nano Particle by Micro Reactor System," http://aiche.confex.com/aiche/s06/preliminaryprogram/abstract_40072.htm (date unknown).
E.F. Paulus, "Molecular and crystal structure of C.I. Pigment Red 208, 12514, n-butyl-2-[2-oxo-3-[N-(2-oxo-2,3-dihydro-5-benzimidazolyl)-carbamoyl]-naphthylidenhydrazino]-benzoat (PV-Rot HF2B),"; Zeitschrift fur *Kristallographie*, vol. 160, pp. 235-243 (1982).
J. van de Streek, et al., "Structures of six industrial benzimidazolone pigments from laboratory powder diffraction data," Acta Crystallographica Section B, Structural Science, 2009, vol. B65, pp. 200-211.
J. Yang et al., "Hydrogen Bonding Control of Self-Assembly: Simply Isophthalic Acid Derivatives Form Cyclic Hexameric Aggregates", Tet. Lett., 22, pp. 3665-3668 (1994).
S. De Feyter et al., "Toward Two-Dimensional Supramolecular Control of Hydrogen-Bonded Arrays: The Case of Isophthalic Acids," Nano Lett., vol. 3, No. 11, pp. 1485-1488 (2003).
A. Zafar, "Linked Bis-Isophthalic Acid Derivatives as Building Blocks in the Design of Self-Assembling Structures," Tet. Lett., vol. 37, No. 14, pp. 2327-2330 (1996).
J. N. Moorthy et al., "Helical Self-Assembl;y of Substituted Benzoic Acids: Influence of Weaker X-X and C-H-X Interactions," J. Am. Chem. Soc., 124, pp. 6530-6531 (2002).
V. K. Potluri et al., "Isophthalic Acid-Derived Organogelators," J. Supramol. Chem., vol. 2, pp. 321-326 (2002).
S. R. Nam et al., "Self-Assembled Organogels Based on Two-Component System," Tetrahedron, vol. 64, pp. 10531-10537 (2008).
H. Y. Lee et al., "Microtubule Formation Using Two-Component Gel System," J. Am. Chem. Soc. vol. 129, pp. 1040-1041 (2007).
O. Lebel et al., "A New Class of Selective Low-Molecular-Weight Gelators Based on Salts of Diaminotriazinecarboxylic Acids," Chem. Mater., vol. 18, pp. 3616-3626 (2006).
H- Y. Hu et al., "Organogels Derives From Potassium 8-Nitroquinolinecarboxylate," Chin. J. Chem., vol. 25, pp. 1389-1393 (2007).
U.S. Appl. No. 12/405,079, filed Mar. 16, 2009.
U.S. Appl. No. 12/509,161, filed Jul. 24, 2009.
U.S. Appl. No. 12/581,488, filed Oct. 19, 2009.
U.S. Appl. No. 12/581,510, filed Oct. 19, 2009.
U.S. Appl. No. 12/581,420, filed Oct. 19, 2009.
U.S. Appl. No. 12/044,613, filed Mar. 7, 2008.
Nov. 29, 2011 Supplemental European Search Report issued in corresponding European Application No. 10170214.0.
Feb. 23, 2012 Office Action issued in U.S. Appl. No. 13/185,058.
Mar. 9, 2012 Office Action issued in U.S. Appl. No. 13/193,326.
Mar. 9, 2012 Office Action issued in U.S. Appl. No. 13/189,887.
Feb. 15, 2012 Office Action issued in U.S. Appl. No. 12/777,329.
CAS Accession No. 2005:1009157 (Document No. 143:434968), Bao et al., "Behaviour of Nucleotides and Oligonucleotides in Potentiometric HPLC Detection", Analytica Chimica Acta (2005) 550(1-2), 130-136.
CAS Accession No. 2002:315164 (Document No. 136:342593), Ushio et al., WO 2002033162 A 1 (Apr. 2002).
CAS Accession No. 1950:16130 (Document No. 44:16130), Carey et al., "Relation of Chemical Constitution of a Series of Esters of Picolinic Acid to Toxicity as Insecticides", Journal of Econonic Entomology (1949), 42, 798-801.
CAS Accession No. 2004:976866 (Document No. 142:130050), Steinkamp et al., "Detection Scheme for Bioassays Based on 2,6-pyridinedicarboxylic acid Derivatives and Enzyme Amplified Lanthanide Luminescence", Analytica Chicmica Acta (2004), 526(1),27-34.
CAS Accession No. 1940:10519 (Document No. 34:10519), "Long-Chain Alkyl Derivatives of 2-aminopyridine", Journal of the Chemical Society (1939), 1855-7.
CAS Accession No. 2004:680170 (Document No. 141:197407), Sano, "Reversible Thermal Recording Material Containing Leuco Dye and Developer", JP2004230720 A (Aug. 2004).
CAS Accession No. 1980:77233 (Document No. 92:77233), Gibalewicz et al., "Study of the Electric Conductivity of Poly(vinylchloride) With Organic Additives", Polimery (Warsaw, Poland) (1979),24(9),325-9.
CAS Accession No. 1988:501769 (Document No. 109:101769), Kaneko, JP63-085548A (Apr. 1988).
CAS Accession No. 2006:889233 (Document No. 145:272901), Harashina, "Polyacetal Compositions for Prevention of Formaldehyde Release and Their Moldings", JP 2006225550 (Aug. 2006).
CAS Accession No. 1997:118989 (Document No. 126:137662), Oota, "Manufacture of Electrostatic Charge Image Development Toners by Suspension Polymerization With Uniform Size Distribution," JP08305084 (Nov. 1996).
CAS Accession No. 2005:1259726 (Document No. 144:6578), Snow et al., "Substituted N-Aryl Benzamides and Related Compounds for Treatment of Amyloid Diseases and Synucleinopathies, Their Preparation and Pharmaceutical Compostions", WO2005113489 (Dec. 2005).
CAS Accession No. 2006:597708 (Document No. 145:64647), Tsujimura et al., "Ink Sets With Good Bleeding Resistance, Ink-Jet Recording Method Using Them and Recorded Materials by the Method", JP2006160815 (Jun. 2006).
CAS Accession No. 1981:605407 (Document No. 95:605407), Pawelec et al., Benzimadazole Azo Pigments, PL105225 (Sep. 1979).
CAS Accession No. 1980:496794 (Document No. 93:96794), Fuchs, "Monoazo Dyes and Their Use", DE 2847285 (May 1980).
CAS Accession No. 1979:422411 (Document No. 91 :22411), Ciba Geigy, "Azo Pigments", JP 54029334 (Mar. 1979).
CAS Accession No. 2005:346583 (Document No. 142:393811), Shakhnovichl, "Azo Pigments for Aqueous Jet-Printing Ink Dispersion and Method for Manufacture of the Inks", US20050081749 A1 (Apr. 2005).
CAS Accession No. 2002:77478 (Document No. 136:134986), Sato et al., Japanese Patent Specification No. JP2002-030091 A (Jan. 2002).
CAS Accession No. 1999:474880 (Document No. 131 :177582), Lee et al., "Controlling the Crystal Morphology of One-Dimensional Tunnel Structures: Induced Crystallization of Alkane/Urea Inclusion Compounds as Hexagonal Flat Plates", Chemical Physics Letters (1999), 307(5,6), 327-332.
CAS Accession No. 1995:568916 (Document No. 122:291987, Boelune et al., Journal of the American Chemical Society (1995), 117(21), 5824-8.
CAS Accession No. 1977:91891 (Document No. 86:91891), Matsuo et al., Japanese Patent Specification No. JP51-134729 (Nov. 1976).
Jun. 13, 2012 Office Action issued in U.S. Appl. No. 13/185,058.
Jun. 15, 2012 Office Action issued in U.S. Appl. No. 13/193,326.
Jun. 21, 2012 Office Action issued in U.S. Appl. No. 13/189,887.
Schwiebert et al., "Engineering the Solid State with 2-Benzimidazolones," J. Am. Chem. Soc., vol. 11, No. 17, pp. 4018-4029, May 1, 1996.
Sep. 25, 2012 Canadian Office Action issued in Canadian Patent Application No. 2,717,579.
Dec. 10, 2012 Office Action issued in U.S. Appl. No. 13/193,326.
Accession No. 1971:46197, abstract of Buehler et al., article entitled: "Metal Complexes with α,ω-bis(2-pyridyl)alkanes," Chimia (1970), 24(12), 433-436.
Accession No. 1983:129983, abstract of European Patent Application No. EP57797 (Aug. 1982).
Accession No. 2005:106034, abstract of Xie et al., article entitled: "New silver(I) coordination architectures of pyridyl dithioether ligands with Ag•••Ag, Ag•••O, Ag•••S and C-H•••F weak interactions," Polyhedron (2005), 24(3), 413-418.

(56) References Cited

OTHER PUBLICATIONS

Accession No. 2005:142281, abstract of Schmuch et al., article entitled: "Amino acid binding by 2-(guanidiniocarbonyl)pyridines in aqueous solvents: a comparative binding study correlating complex stability with stereoelectronic factors," Chemistry—a European Journal (2005), 11(4), 1109-1118.

Accession No. 2006:274394, abstract of Pellei et al., article entitled: "Synthesis and characterization of new organotin(IV) complexes with polyfunctional ligands," Journal of Organometallic Chemistry (2006), 691(8), 1615-1621.

Accession No. 2006:1202500, abstract of PCT International Application No. WO 2006/122156 A2 (Nov. 2006).

Accession No. 2007:488296, abstract of Yu et al., article entitled: "N1, N3-Di-2-pyridylmalonamide," Acta Crystallographica, Section E: Structure Reports Online (2007), E63(5), o2650.

Nov. 15, 2012 Office Action issued in U.S. Appl. No. 13/185,058.

Mar. 22, 2012 Canadian Office Action issued in Canadian Application No. 2,717,464.

* cited by examiner

SELF-ASSEMBLED NANOSTRUCTURES

TECHNICAL FIELD

This disclosure is generally directed to amphiphilic organic compounds with hydrogen-bonding (H-bonding) functionalities that can reversibly self-assemble into well-defined nanostructures, and methods of forming these self-assembled nanostructures. More specifically, the present disclosure relates to amphiphilic alkylated derivatives of aromatic acids and self-assembled nanostructures generated therefrom. These nanostructures include a variety of different nanoparticle morphologies, often described as spherical shaped particles, planar sheets, or pseudo one-dimensional structures such as fibrils, ribbons, tapes, tubes, rods, belts, etc. Another objective of this disclosure is to provide compositions containing the above mentioned nanostructures from alkylated derivatives of aromatic acids, which are either individually dispersed (e.g. free standing), or organized as building blocks to even higher order structures such as three-dimensional (3D) network (e.g., organogels or xerogels) or anisotropic materials (e.g. liquid crystals) for a wide variety of uses.

CROSS-REFERENCE TO RELATED APPLICATIONS

Disclosed in U.S. patent application Ser. No. 12/405,079 filed Mar. 16, 2009, and Ser. No. 12/044,613 filed Mar. 7, 2008, both to Rina Carlini et al. is a nanoscale pigment particle composition, comprising: a benzimidazolone pigment, and a sterically bulky stabilizer compound associated non-covalently with the benzimidazolone pigment; wherein presence of the stabilizer limits an extent of particle growth and aggregation, to afford nanoscale pigment particles. Also disclosed is a process for preparing nanoscale particles of benzimidazolone pigments, comprising: providing one or more organic pigment precursor precursors to a benzimidazolone pigment comprising a benzimidazolone moiety, providing a solution or suspension of a sterically bulky stabilizer compound that associates non-covalently with the benzimidazolone moiety on one of the pigment precursors, and carrying out a chemical reaction to form a benzimidazolone pigment composition comprising nanoscale pigment particles, whereby the pigment precursors are incorporated with the benzimidazolone pigment and one or more functional moieties on the benzimidazolone pigment is non-covalently associated with the steric stabilizer, so as to limit the extent of particle growth and aggregation and result in nanoscale pigment particles.

Disclosed in U.S. patent application Ser. No. 12/581,420 filed Oct. 19, 2009, to Rina Carlini et al. is a nanoscale pigment particle composition, comprising: a benzimidazolone pigment, and a sterically bulky stabilizer compound associated non-covalently with the benzimidazolone pigment, wherein the sterically bulky stabilizer compound comprises an aromatic acid derivative; wherein the presence of the associated stabilizer limits an extent of particle growth and aggregation, to afford nanoscale pigment particles.

Disclosed in U.S. patent application Ser. No. 12/509,161 filed Jul. 24, 2009, to Rina Carlini et al. is a process for preparing nanoscale particles of benzimidazolone pigments, comprising: providing one or more organic pigment precursor to a benzimidazolone pigment, providing a solution or suspension of a sterically bulky stabilizer compound that associates non-covalently with a benzimidazolone moiety on one of the pigment precursors, wherein the sterically bulky stabilizer compound is selected from the group consisting of substituted pyridine derivatives, alkylated benzimidazolone compounds, alkylated derivatives of aromatic acids, and mixtures thereof, and carrying out a coupling reaction to form a benzimidazolone pigment composition, whereby the pigment precursors are incorporated within the benzimidazolone pigment and one or more functional moieties on the benzimidazolone pigment is non-covalently associated with the sterically bulky stabilizer, so as to limit an extent of particle growth and aggregation and result in nanoscale pigment particles.

The entire disclosures of the above-mentioned applications are totally incorporated herein by reference.

BACKGROUND

Recent technology trends in materials science indicate that the use of nanotechnology-enabled components and materials are gaining more appeal due to the enhanced (and sometimes even breakthrough) performance being exhibited. Functional nanomaterials exhibit many unique and often tunable physical and chemical properties that are different than those of their bulk counterparts. Developments have been recently made towards the fabrication of nanomaterials having well defined shape and dimensions involving either "top down" or "bottom up" fabrication strategies. "Top down" approaches involve cutting down larger structures into the desired shape with the desired dimensions (e.g. nanolithography). "Bottom up" strategies involve growing structures of the desired shape and dimensions from smaller building blocks (e.g. self-assembly). The latter is the preferred approach because it is much more efficient and bypasses the need for cost-intensive and energy-intensive fabrication processes.

Molecular self-assembly is a practical "bottom up" approach to arrive at nanostructured materials. In this approach, self-complementary molecules are designed as 'building blocks' with a specific size, shape and at least one functional group, to aggregate in an ordered manner. The resulting ensemble often possesses completely different properties than their smaller building subunits. However, the challenge of this approach is to design the appropriate molecular subunits that can assemble into useful nanostructures in a controlled manner such that the final desired size and shape can be achieved. Consequently, the modular use of hydrogen-bonding molecular building blocks is key to designing novel nanoscale supramolecular structures, non-covalent polymers, organogelators, and liquid crystals, that have useful properties for developing advanced functional materials such as for example adhesives, self-healing coatings, as well as many others.

Amphiphilic alkylated benzoic acid (BA), phthalic acid (PA), and isophthalic acid (ISA) derivatives are known to self-assemble into supramolecular aggregates through hydrogen-bonding either in solution (see, J. Yan, J.-L. Marendaz, S. J. Geib, A. D. Hamilton, *Tet. Lett.* 1994, 22, 3665-3668), as physio-absorbed monolayers on surfaces (see, S. De Feyter, A. Gesquiere, M. Klapper, K. Mullen, F. C. De Schryver, *Nano Lett.* 2003, 3, 11, 1485-1488), or in the solid state (see, A. Zafar, J. Yang, S. J. Geib, A. D. Hamilton, *Tet. Lett.* 1996, 37, 14, 2327-2330). Benzoic acids primarily undergo self-association to form either hydrogen-bonded dimer or catemer motifs (see, J. N. Moorthy, R. Natarajan, P. Mal, P. Venugopalan, *J. Am. Chem. Soc.* 2002, 124, 6530-6531.) For isophthalic acid derivatives, linear tapes/ribbons and cyclic rosette hydrogen bonding motifs have been observed for different derivatives either deposited on surfaces by STM or in solid state crystal structures (see, Zafar (above), and V. K. Potluri, A. D. Hamilton, *J. Supramol. Chem.* 2002, 2, 321-326). As described in Potluri (above), the cyclic motif is typically favored with bulkier 5-substituents (i.e., a decyloxy group, or benzhydryloxyundecyloxy), which disrupt the crystalline side-chain packing stabilizing the linear arrangements.

Some exemplary reported benzoic acid and isophthalic acid derivatives incorporate linear alkyl groups with limited lengths (1-20 carbons). Other reported benzoic acid and isophthalic acid derivatives, such as having multiple or branched alkyl chains, are described in Zafar (above), Potluri (above), and S. De Feyter (above). Some alkylated benzoic acid, and isophthalic acid organogelators are also reported. Specific examples of alkylated benzoic acid organogelators include Hong's benzoic acids, for examples, in S. R. Nam, H. Y. Lee, J-I. Hong, *Tetrahedron* 2008, 64, 10531-10537, and H. Y. Lee, S. R. Nam, J-I. Hong, *J. Am. Chem. Soc.* 2007, 129, 1040-1041. Specific examples of alkyloxy isophthalic acid organogelators include Hamilton's urea (Potluri, above), 1,2, 3-tridecyloxybenzyl functionalized isophthalic acid derivatives (Zafar, above). Also, related alkali salts of alkylated derivatives of aromatic acids as organogelators include, for example, O. Lebel, M-E. Perron, T. Maris, S. F. Zalzal, A. Nanci, J. D. Wuest, *Chem. Mater.* 2006, 18, 3616-3626, and H-Y. Hu, Y. Yang, J-F. Xiang, C-F. Chen, *Chin. J. Chem.* 2007, 25, 1389-1393.

The appropriate components and process aspects of each of the foregoing may be selected for the present disclosure in embodiments thereof, and the entire disclosure of the above-mentioned references are totally incorporated herein by reference.

However, there remains a need for new and improved nanotechnology-enabled components and materials, particularly those having self-complementary functional groups which can self-assemble readily by a "bottom up" fabrication strategy to produce well-defined nanostructures and potentially higher-order network structures, that can be useful and desirable properties in developing functional materials.

SUMMARY

The present disclosure addresses these and other needs, by providing alkylated derivatives of aromatic acids and self-assembled nanostructures formed from such alkylated derivatives of aromatic acids.

In an embodiment, the present disclosure provides nanostructures formed from alkylated derivatives of aromatic acids of the formula:

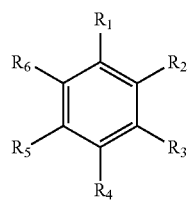

wherein at least one of $R_1$ to $R_6$ represents a carboxylic acid group, a primary amide group, an ester group, an amidine group, or a salt thereof, at least one other of $R_1$ to $R_6$ is X—$R_c$, and the remaining of $R_1$ to $R_6$ independently represent H or substituted or unsubstituted organic groups;

X represents a linking group; and $R_c$ represents a substituted or unsubstituted alkyl group.

DETAILED DESCRIPTION OF EXEMPLARY EMBODIMENTS

Figure 1:
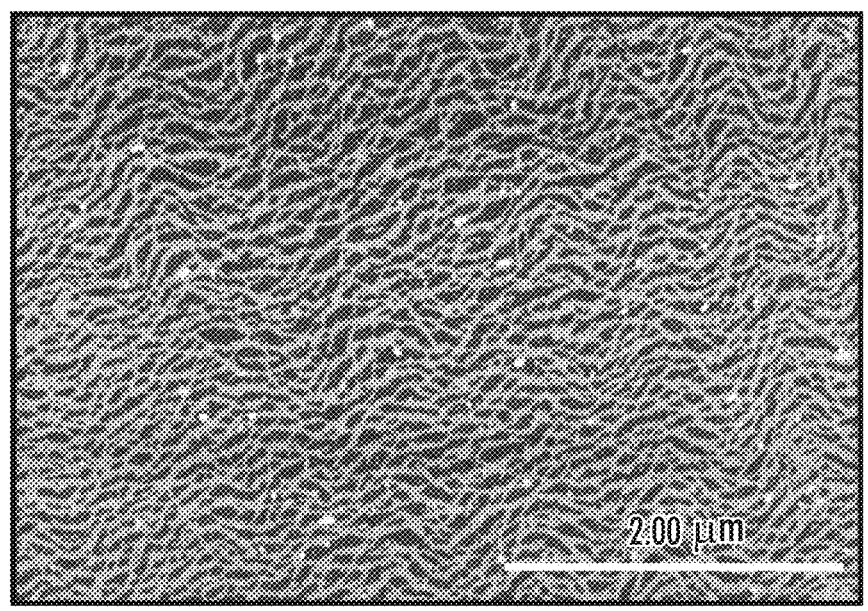
FIG. 1 shows an STEM image of a material of Example 1.

Terms, when used in this application, have their common meaning unless otherwise stated.

The term "nanostructure" shall refer to a physical structure (e.g. a particle or the like), which, in at least one dimension, such as the smallest dimension, has a size ranging from about 1 or about 10 or about 20 to about 100 or to about 200 or to about 500 nm, such as between about 10 to about 300 nm, and which has a largest dimension that is desirably less than about 5000 nm in size, such as less than about 2000 nm in size, or less than about 1000 nanometers in size.

The term "1D structure" shall refer to a structure having a significantly larger length than height or width (or diameter). The aspect ratio, defined as length divided by the width can be at least about 5 or at least about 10, such as about 100-500. These 1D structures can thus take the form of strings (which in the case of being electrically conductive may be referred to as wires), tapes, or the like.

The term "2D structure" shall refer to a flat, planar structure having length and width that are comparable in size, but no depth (or negligible depth). The aspect ratio can be at most about 5, such as about 2, or about 1. "2D Structures" may be either porous or non porous sheet structures (e.g. a film or wafer).

The term "3D structure" shall refer to a structure that possesses the dimensions of length, width, and height that are comparable and appreciable in relative size. In the context of this disclosure, the term "3D structure" refers to a higher order arrangement of smaller (more elementary) nanostructures; i.e. 1D structures. 3D structures may include porous networks like, for example a gel network, or even more highly ordered, less porous networks such as liquid crystals.

The term "nanofibril" shall refer to a 1D structure resembling a long slender filament or fiber with diameter desirably less than about 100 nm size, such as less than about 50 nm in size, or less than about 20 nm in size. The length of the nanofibril can range from about 20 nm up to about 5000 nm or larger.

The term "nanofiber" shall refer to a 1D structure resembling a thick filament or fiber with a diameter desirably less than about 200 nm in size, or less than about 100 nm, or about 50 nm in size. "Nanofibers" in the context of this disclosure may consist of a single structural element or may be composed of more than one structural element, such as a bundle of smaller "nanofibrils".

Embodiments of the present disclosure provide alkylated derivatives of aromatic acids and self-assembled nanostructures formed from such alkylated derivatives of aromatic acids.

The alkylated derivatives of aromatic acids have the function of self-assembling into larger structures, either alone or in combination with other materials. For example, the compounds can be used to self-assemble with colorant molecules to form a nanoscale pigment particle composition, such as disclosed in U.S. patent application Ser. No. 12/405,079 filed Mar. 16, 2009, incorporated by reference above. The alkylated derivatives of aromatic acids may thus limit the extent of primary particle aggregation and growth, so as to produce predominantly nanoscale particles. Multiple molecules of the alkylated derivatives of aromatic acids, which may be the same or different, may also self-assemble with each other to form larger 1-, 2-, or even 3-dimensional structures.

Generally, the alkylated derivatives of aromatic acids have a hydrocarbon moiety that provides sufficient steric bulk to enable the function of the compound to regulate particle size of the aggregated structures. The hydrocarbon moiety in embodiments is predominantly aliphatic, but in other embodiments can also incorporate aromatic groups, and generally contains at least 6 carbon atoms, such as at least 12 carbons or at least 16 carbons, and not more than about 100 carbons, but the actual number of carbons can be outside of these ranges. The hydrocarbon moiety can be either linear, cyclic or branched, and in embodiments is desirably branched, and may or may not contain cyclic moieties such as cycloalkyl rings or aromatic rings. The aliphatic branches are long with at least 2 carbons in each branch, such as at least 6 carbons in each branch, and not more than about 100 carbons.

It is understood that the term "steric bulk" is a relative term, based on comparison with the size of other compounds to which the alkylated derivatives of aromatic acids may become non-covalently associated. In embodiments, the phrase "steric bulk" refers to the situation when the hydrocarbon moiety of the compound that participates in the hydrogen bonding, occupies a 3-dimensional spatial volume that effectively prevents the approach or association of other chemical entities. As examples, the following hydrocarbon moieties on the alkylated derivatives of aromatic acids in embodiments may be considered to have adequate "steric bulk" so as to enable the compound to limit the extent of self-assembly or aggregation and mainly produce nanoscale structures:

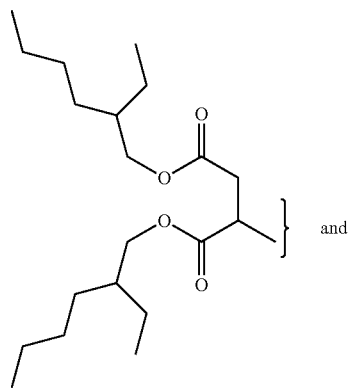

-continued

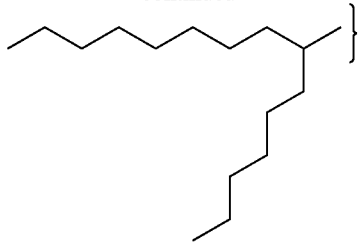

Suitable alkylated derivatives of aromatic acids are desirably those that are amphiphilic; that is, they have a hydrophilic or a polar functional group with available heteroatoms for H-bonding with target molecules, as well as a non-polar or hydrophobic sterically bulky group that has at least 6 carbons and not more than 100 carbons and is predominantly aliphatic (linear, branched or cyclic) groups but can include some ethylenically unsaturated groups and/or aryl groups.

Representative examples of suitable alkylated derivatives of aromatic acids include (but are not limited to) compounds of the following general Formula:

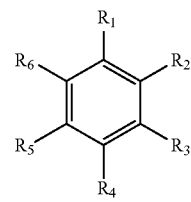

wherein at least one of $R_1$ to $R_6$ represents a carboxylic acid group, a primary amide group, an ester group, an amidine group, or a salt thereof, at least one other of $R_1$ to $R_6$ is X—$R_c$, and the remaining of $R_1$ to $R_6$ independently represent H or substituted or unsubstituted organic groups;

X represents a linking group; and $R_c$ represents a substituted or unsubstituted alkyl group.

Also encompassed by the above formula are compounds where two adjacent groups of $R_1$ to $R_6$ form a cyclic amide structure, such as of the following formula:

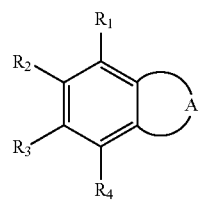

where $R_1$ to $R_4$ are as defined above and A represents a moiety comprising one or more functional groups such as —C(=O)—NH—C(=O)—, —NH—C(=O)—O—, or the like.

In the above formula, the groups that represent substituted or unsubstituted organic groups are not particularly limited, and can be suitably provided to provide desired results. Suitable groups include a substituted or unsubstituted alkyl group, a substituted or unsubstituted aryl group, a substituted or unsubstituted aryl-alkyl group, a substituted or unsubstituted alkyl-aryl group, or the like, where the substitutions can be, for example, hydrocarbon groups, substituted hydrocarbon groups, heteroatoms, halogens, or the like.

At least one of the groups $R_1$ to $R_6$ represents a carboxylic acid group, a primary amide group, an ester group, an amidine group, or a salt thereof. Suitable groups include —COOH, —CONH$_2$, —COO, —(C=NH)—NH$_2$, and salts thereof, such as alkali salts, salts with quaternary alkyl amines, and the like. In one embodiment, only one of $R_1$ to $R_6$ represents a carboxylic acid group, a primary amide group, an ester group, an amidine group, or a salt thereof, such as a carboxylic acid group or a primary amide group; in other embodiments, two or three of $R_1$ to $R_6$ can independently represent a carboxylic acid group, a primary amide group, an ester group, an amidine group, or a salt thereof, such as a carboxylic acid group or a primary amide group. Where two or more carboxylic acid groups or primary amide groups are present in one molecule, those groups can be at any of $R_1$ to $R_6$, and thus can be at adjacent positions or can be at non-adjacent positions. Thus, two groups can be at positions 1,2; 1,3; 1,4; or the like, while three groups can be at positions 1,2,3; 1,2,4; 1,3,4; 1,3,5; or the like.

In a similar manner, at least one of the groups $R_1$ to $R_6$ represents X—$R_c$. In one embodiment, only one of $R_1$ to $R_6$ represents X—$R_c$; in other embodiments, two, three, four, or five of $R_1$ to $R_6$ can independently represent X—$R_c$. Where two or more X—$R_c$ groups are present in one molecule, those groups can be at any of $R_1$ to $R_6$, and thus can be at adjacent positions or can be at non-adjacent positions. Furthermore, the X—$R_c$ group, or one or more of the X—$R_c$ groups when more than one is present, can be adjacent to one or more of the carboxylic acid groups, primary amide groups, an ester group, an amidine group, or a salt thereof, or can be non-adjacent to such groups.

In some embodiments, one of more, such as one, two, three, or four, of $R_1$ to $R_6$ can represent H. However, in other embodiments, such as where hydrogen bonding can occur between other moieties of the compound, all of $R_1$ to $R_6$ can represent groups other than H, as described above.

In one exemplary embodiment, one of $R_1$ to $R_6$ represents a carboxylic acid group or a primary amide group, such as a carboxylic acid group, and two of $R_1$ to $R_6$ independently represent X—$R_c$. For example, $R_1$ represents a carboxylic acid group or a primary amide group, such as a carboxylic acid group, and $R_3$ and $R_5$ independently represent X—$R_c$.

In another exemplary embodiment, two of $R_1$ to $R_6$ independently represent a carboxylic acid group or a primary amide group, such as both represent a carboxylic acid group or both represent a primary amide groups, and one of $R_1$ to $R_6$ represents X—$R_c$. For example, $R_1$ and $R_3$ independently represent a carboxylic acid group or a primary amide group, such as both represent a carboxylic acid group or both represent a primary amide groups, and $R_c$ represents X—$R_c$.

The linking group X can be any suitable functional group that connects the substituted or unsubstituted alkyl group $R_c$ to the aromatic acid moiety. Examples of suitable linking groups include —O—, —S—, —SO—, —SO$_2$—, amide groups (—NH—(C=Z)—) and (—(C=Z)—NH—), amine groups (—NH—), urea groups (—NH—(C=Z)—NH—), carbamate or urethane groups (—NH—(C=Z)—O—) and (O—(C=Z)—NH—), carbonate groups, and ester groups (—(C=Z)—O—) or (—O—(C=Z)—), where heteroatom Z can be either O or S.

The groups $R_1$ to $R_6$ that are not H or the carboxylic acid group, primary amide group, ester group, amidine group, or salts thereof, including the $R_c$ group, can be any suitable alkyl group that can provide a sterically bulky layer when the compounds are structurally aggregated, thereby preventing or limiting the approach of other particles or molecules that leads to uncontrolled aggregation and particle growth.

Examples of suitable sterically bulky groups include the various non-polar or hydrophobic sterically bulky groups described previously. Specific examples of the sterically bulky alkyl groups include straight or branched alkyl groups of 1 to about 100, such as 1 to about 50 or 6 to about 30 carbon atoms, and including large linear, branched and/or cyclic aliphatic groups like those of the general formulae:

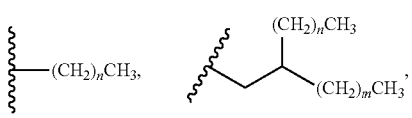

where $n = 0\text{-}49$ where $m = 0\text{-}49$
and $n = m$ or $m + p$
and $p = 1\text{-}10$

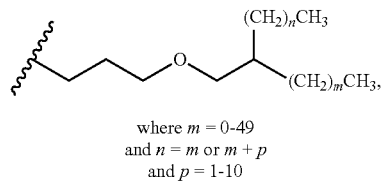

where $m = 0\text{-}49$
and $n = m$ or $m + p$
and $p = 1\text{-}10$

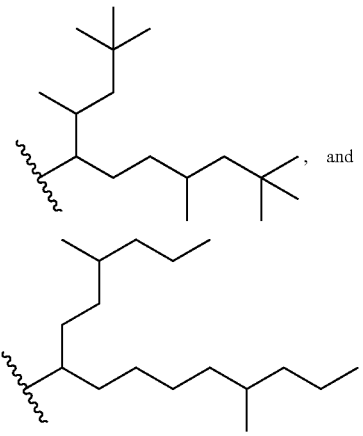

, and

;

and also includes substituted straight or branched alkyl groups of 1 to about 50, such as 1 to about 40 or 6 to about 30 carbon atoms, including those of the formula —CO—(CH$_2$)$_n$—CH$_3$, where n is from 0 to about 30; and the like. Other useful $R_c$ groups may include aliphatic hydrocarbons with higher degrees of branching, cyclic hydrocarbons, as well more polar groups that contain heteroatoms such as O, S, N, including linear or branched alkyleneoxy chains such as oligo- or poly-[ethyleneglycol] and the like.

Thus, for example, the aromatic acid derivatives can be, but are not limited to:

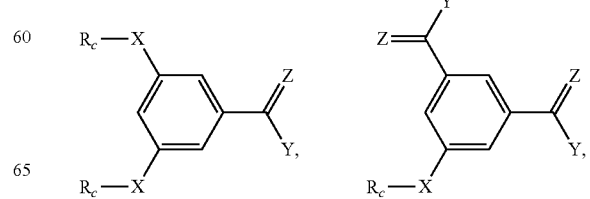

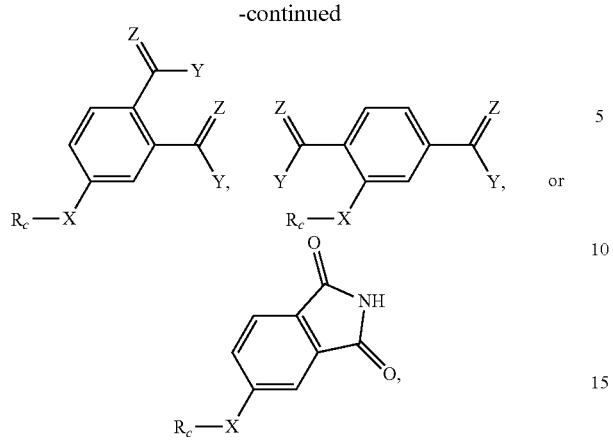

where Y=OH or NH$_2$, where Z=O, NH, or S, and where groups R$_c$ may be the same or different when more than one R$_c$ is present.

In embodiments, the group R$_c$ can also be a difunctional moiety that bridges two or more aromatic acid moieties, as illustrated in the general formula,

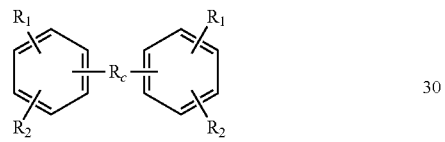

where examples of suitable difunctional groups R$_c$ include —(CH$_2$)$_n$—; —X—(CH$_2$)$_n$X; —[(XCH$_2$CH$_2$)$_n$]X—; —[(C=O)—(CH$_2$)$_n$—(C=O)]—; —X—[(C=O)—(CH$_2$)$_n$—(C=O)]—X—; —X—[(C=O)—X—(CH$_2$)$_n$—X—(C=O)]—X—; —[(C=O)—X—(CH$_2$)$_n$—X—(C=O)]—, wherein X is defined as O, S, —SO—, —SO$_2$—, or NH and integer n is 1 to about 50; and also large branched alkylated functional groups such as:

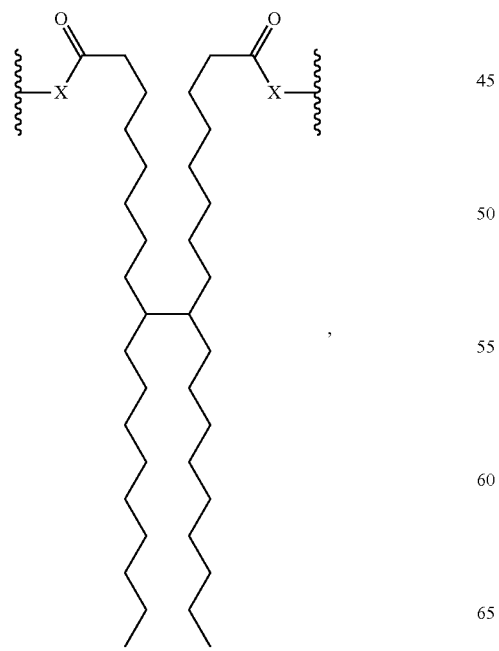

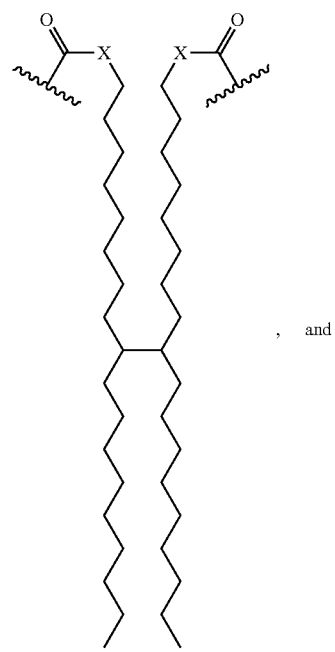

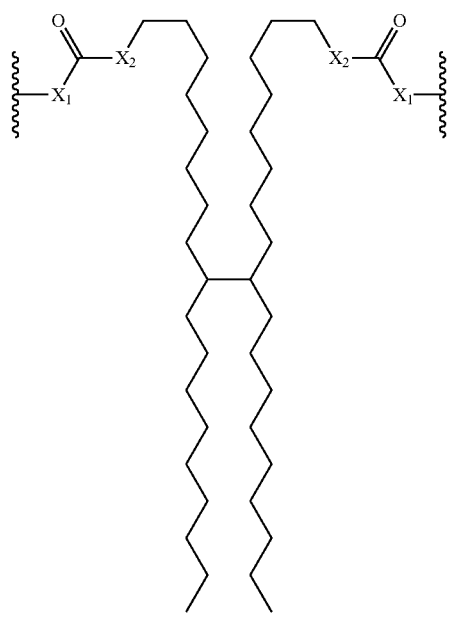

wherein X, X$_1$ and X$_2$ are defined as being either O, S, —SO—, —SO$_2$—, or NH, and X$_1$ and X$_2$ may or may not be the same.

Specific examples of the alkylated benzimidazolone compounds thus include, but are not limited to, those in the following Tables 1, 2, and 3:

TABLE 1
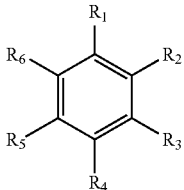
R₄ and R₆ = H
| | R₁ | R₂ | R₃ | R₅ |
|---|---|---|---|---|
| 1 | —COOH | H | 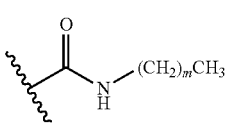 $m = 17$ | 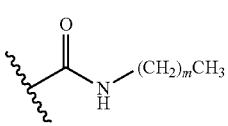 $m = 17$ |
| 2 | —COOH | H | 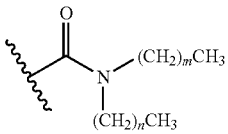 $m = 11, n = 9$ | 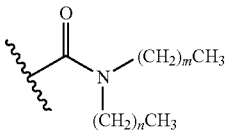 $m = 11, n = 9$ |
| 3 | —COOH | H | 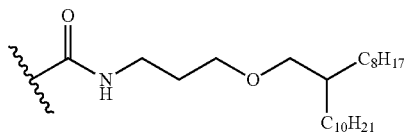 | 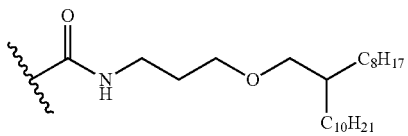 |
| 4 | —COOH | H | 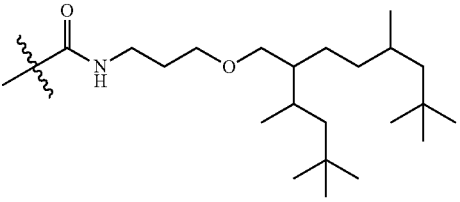 [SMILES: *C(=O)NCCCOCC(CCC(C)CC(C)(C)C)C(C)CC(C)(C)C] | 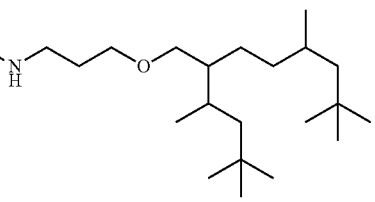 |
| 5 | —COOH | H | 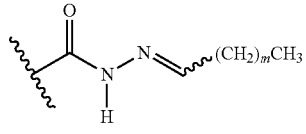 $m = 17$ | 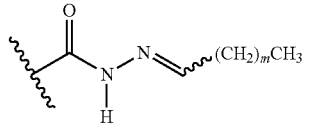 $m = 17$ |
| 6 | —COOH | H | 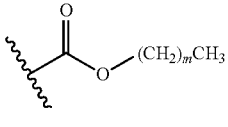 $m = 17$ | 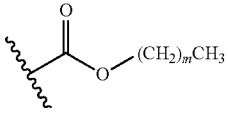 $m = 17$ |
| 7 | —COOH | H | 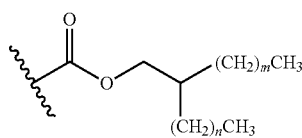 $m = 9, n = 7$ | 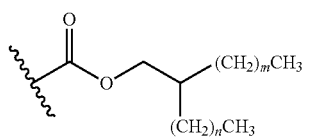 $m = 9, n = 7$ |

TABLE 1-continued
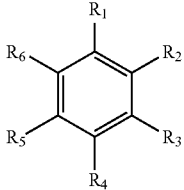
$R_4$ and $R_6$ = H
| | $R_1$ | $R_2$ | $R_3$ | $R_5$ |
|---|---|---|---|---|
| 8 | —COOH | H | 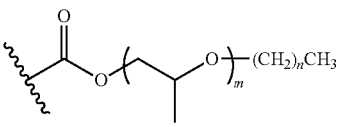<br>m = 2, n = 3<br>m = 3, n = 3 | 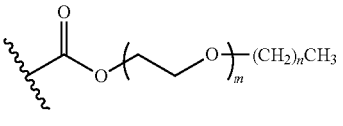<br>m = 2, n = 3<br>m = 3, n = 3 |
| 9 | —COOH | H | 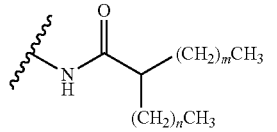<br>m = 1, n = 3<br>m = 2, n = 3 | 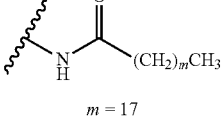<br>m = 1, n = 3<br>m = 2, n = 3 |
| 10 | —COOH | H | 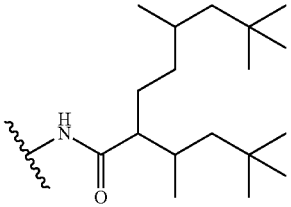<br>m = 11, n = 9<br>m = 7, n = 5<br>m = 5, n = 3 | 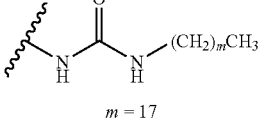<br>m = 11, n = 9<br>m = 7, n = 5<br>m = 5, n = 3 |
| 11 | —COOH | H | 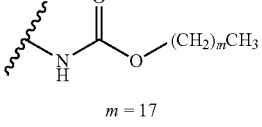<br>m = 17 | <br>m = 17 |
| 12 | —COOH | H | | |
| 13 | —COOH | H | <br>m = 17 | <br>m = 17 |
| 14 | —COOH | H | <br>m = 17 | <br>m = 17 |

TABLE 1-continued
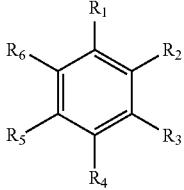
R4 and R6 = H
| | R1 | R2 | R3 | R5 |
|---|---|---|---|---|
| 15 | —COOH | H | 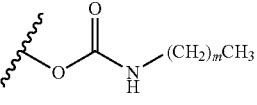<br>$m = 17$ | 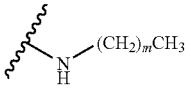<br>$m = 17$ |
| 16 | —COOH | H | 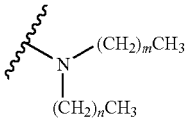<br>$m = 17$ | 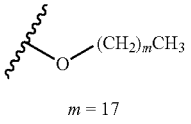<br>$m = 17$ |
| 17 | —COOH | H | 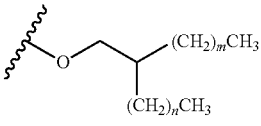<br>$m = 17$ | 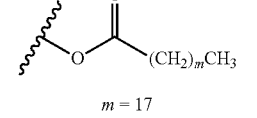<br>$m = 17$ |
| 18 | —COOH | H | 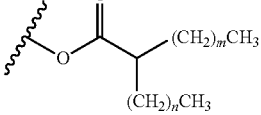<br>$m = 17$ | 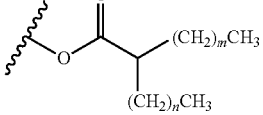<br>$m = 17$ |
| 19 | —COOH | H | $m = 9, n = 7$ | $m = 9, n = 7$ |
| 20 | —COOH | H | $m = 17$ | $m = 17$ |
| 21 | —COOH | H | $m = 11, n = 9$<br>$m = 7, n = 5$<br>$m = 5, n = 3$ | $m = 11, n = 9$<br>$m = 7, n = 5$<br>$m = 5, n = 3$ |

TABLE 1-continued
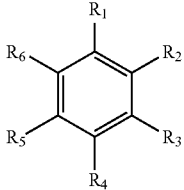
R₄ and R₆ = H
| | R₁ | R₂ | R₃ | R₅ |
|---|---|---|---|---|
| 22 | —COOH | H | 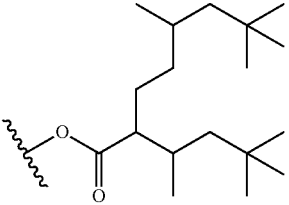 [SMILES: *OC(=O)C(CCC(C)CC(C)(C)C)C(C)CC(C)(C)C] | 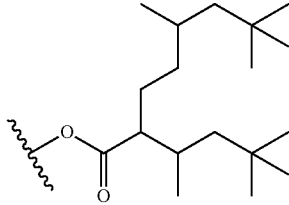 [SMILES: *OC(=O)C(CCC(C)CC(C)(C)C)C(C)CC(C)(C)C] |
| 23 | —CONH₂ | H | 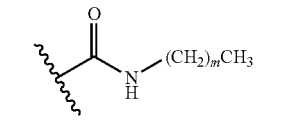 $m = 17$ | 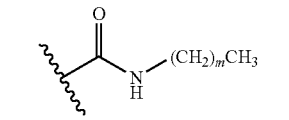 $m = 17$ |
| 24 | —CONH₂ | H | 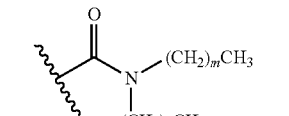 $m = 11, n = 9$ | 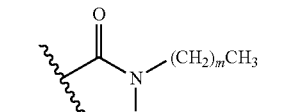 $m = 11, n = 9$ |
| 25 | —CONH₂ | H | 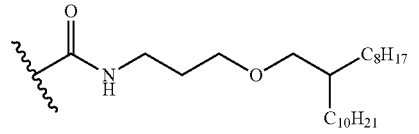 | 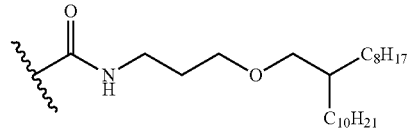 |
| 26 | —CONH₂ | H | 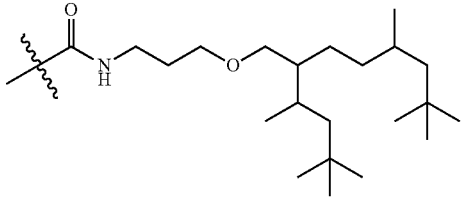 [SMILES: *C(=O)NCCCOCC(CCC(C)CC(C)(C)C)C(C)CC(C)(C)C] | 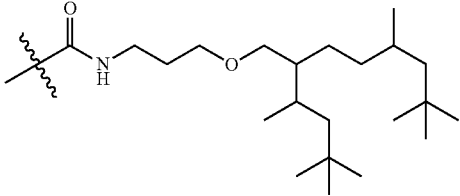 [SMILES: *C(=O)NCCCOCC(CCC(C)CC(C)(C)C)C(C)CC(C)(C)C] |
| 27 | —CONH₂ | H | 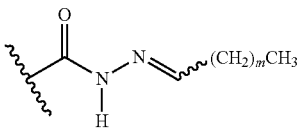 $m = 17$ | 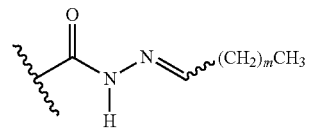 $m = 17$ |
| 28 | —CONH₂ | H | 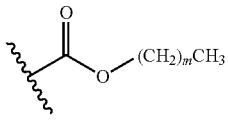 $m = 17$ | 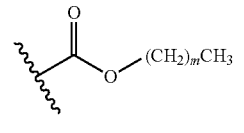 $m = 17$ |

TABLE 1-continued
$R_4$ and $R_6$ = H
| | $R_1$ | $R_2$ | $R_3$ | $R_5$ |
|---|---|---|---|---|
| 29 | —CONH$_2$ | H | 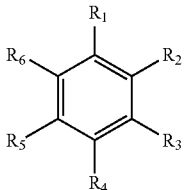 $m = 9, n = 7$ | 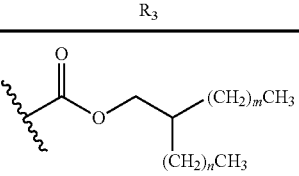 $m = 9, n = 7$ |
| 30 | —CONH$_2$ | H | $m = 2, n = 3$ $m = 3, n = 3$ | $m = 2, n = 3$ $m = 3, n = 3$ |
| 31 | —CONH$_2$ | H | $m = 1, n = 3$ $m = 2, n = 3$ | $m = 1, n = 3$ $m = 2, n = 3$ |
| 32 | —CONH$_2$ | H | 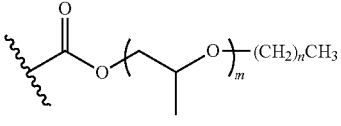 $m = 11, n = 9$ $m = 7, n = 5$ $m = 5, n = 3$ | 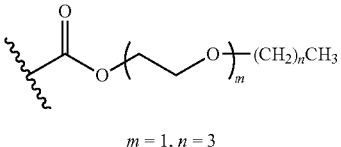 $m = 11, n = 9$ $m = 7, n = 5$ $m = 5, n = 3$ |
| 33 | —CONH$_2$ | H | $m = 17$ | $m = 17$ |
| 34 | —CONH$_2$ | H | 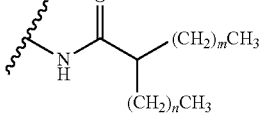 | 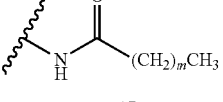 |
| 35 | —CONH$_2$ | H | 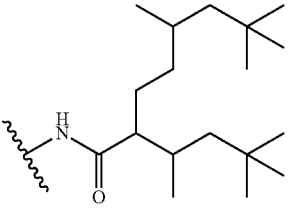 [SMILES: *NC(=O)C(CCC(C)CC(C)(C)C)C(C)CC(C)(C)C] $m = 17$ | 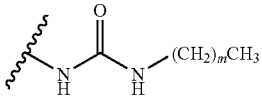 $m = 17$ |

TABLE 1-continued

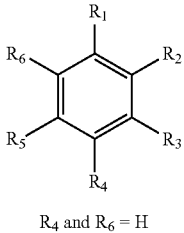

R4 and R6 = H

| | R1 | R2 | R3 | R5 |
|---|---|---|---|---|
| 36 | —CONH₂ | H | 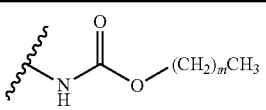 carbamate –NH–C(O)–O–(CH₂)ₘCH₃, m = 17 | carbamate –NH–C(O)–O–(CH₂)ₘCH₃, m = 17 |
| 37 | —CONH₂ | H | carbamate –O–C(O)–NH–(CH₂)ₘCH₃, m = 17 | carbamate –O–C(O)–NH–(CH₂)ₘCH₃, m = 17 |
| 38 | —CONH₂ | H | –NH–(CH₂)ₘCH₃, m = 17 | –NH–(CH₂)ₘCH₃, m = 17 |
| 39 | —CONH₂ | H | –N[(CH₂)ₘCH₃][(CH₂)ₙCH₃], m = 17 | –N[(CH₂)ₘCH₃][(CH₂)ₙCH₃], m = 17 |
| 40 | —CONH₂ | H | –O–(CH₂)ₘCH₃, m = 17 | –O–(CH₂)ₘCH₃, m = 17 |
| 41 | —CONH₂ | H | –O–CH₂–CH[(CH₂)ₘCH₃][(CH₂)ₙCH₃], m = 9, n = 7 | –O–CH₂–CH[(CH₂)ₘCH₃][(CH₂)ₙCH₃], m = 9, n = 7 |
| 42 | —CONH₂ | H | –O–C(O)–(CH₂)ₘCH₃, m = 17 | –O–C(O)–(CH₂)ₘCH₃, m = 17 |
| 43 | —CONH₂ | H | –O–C(O)–CH[(CH₂)ₘCH₃][(CH₂)ₙCH₃], m = 11, n = 9; m = 7, n = 5; m = 5, n = 3 | –O–C(O)–CH[(CH₂)ₘCH₃][(CH₂)ₙCH₃], m = 11, n = 9; m = 7, n = 5; m = 5, n = 3 |

TABLE 1-continued
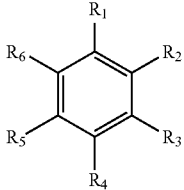
R4 and R6 = H
| | R₁ | R₂ | R₃ | R₅ |
|---|---|---|---|---|
| 44 | —CONH₂ | H | 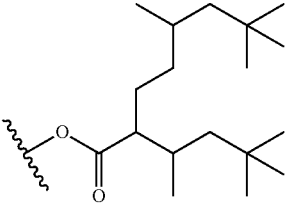 [SMILES: *OC(=O)C(CCC(C)CC(C)(C)C)C(C)CC(C)(C)C] | 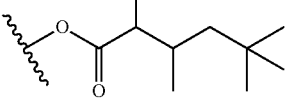 |
| 45 | —COOH | H | —COOH | 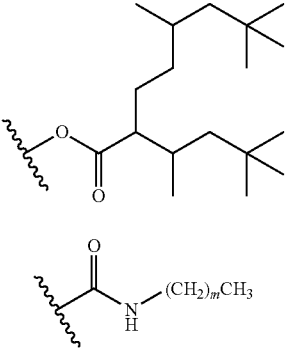<br>m = 17 |
| 46 | —COOH | H | —COOH | 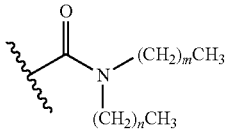<br>m = 11, n = 9 |
| 47 | —COOH | H | —COOH | 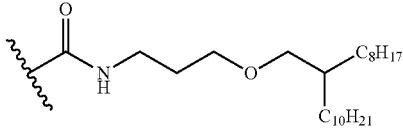 |
| 48 | —COOH | H | —COOH | 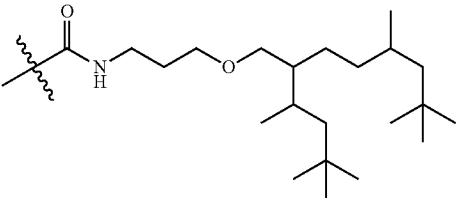 [SMILES: *C(=O)NCCCOCC(CCC(C)CC(C)(C)C)C(C)CC(C)(C)C] |
| 49 | —COOH | H | —COOH | 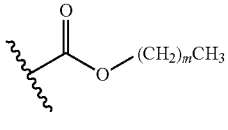<br>m = 15 |
| 50 | —COOH | H | —COOH | 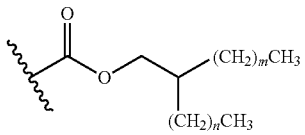<br>m = 9, n = 7 |

TABLE 1-continued
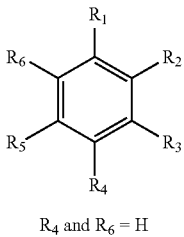
R4 and R6 = H
| | R1 | R2 | R3 | R5 |
|---|---|---|---|---|
| 51 | —COOH | H | —COOH | 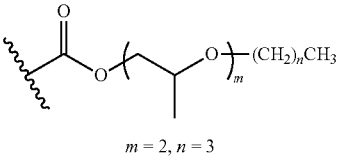<br>$m = 2, n = 3$<br>$m = 3, n = 3$ |
| 52 | —COOH | H | —COOH | 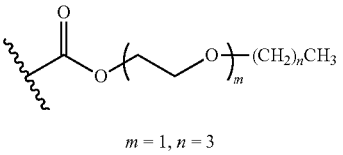<br>$m = 1, n = 3$<br>$m = 2, n = 3$ |
| 53 | —COOH | H | —COOH | 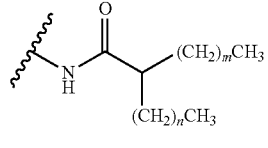<br>$m = 11, n = 9$ |
| 54 | —COOH | H | —COOH | 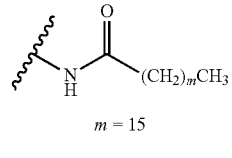<br>$m = 15$ |
| 55 | —COOH | H | —COOH | 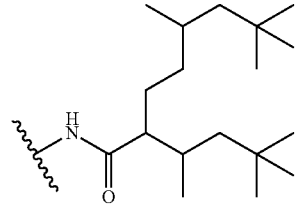 [SMILES: *NC(=O)C(CCC(C)CC(C)(C)C)C(C)CC(C)(C)C] |
| 56 | —COOH | H | —COOH | 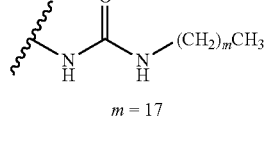<br>$m = 17$ |
| 57 | —COOH | H | —COOH | 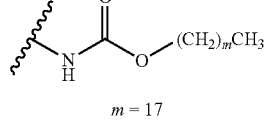<br>$m = 17$ |

TABLE 1-continued
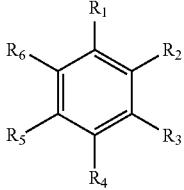
R$_4$ and R$_6$ = H
| | R$_1$ | R$_2$ | R$_3$ | R$_5$ |
|---|---|---|---|---|
| 58 | —COOH | H | —COOH | 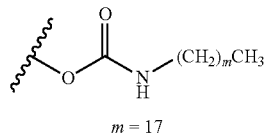<br>$m = 17$ |
| 59 | —COOH | H | —COOH | 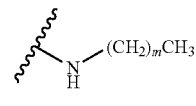<br>$m = 17$ |
| 60 | —COOH | H | —COOH | 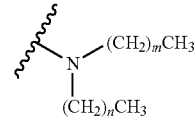<br>$m = 17$ |
| 61 | —COOH | H | —COOH | 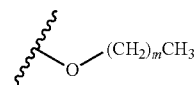<br>$m = 16$ |
| 62 | —COOH | H | —COOH | 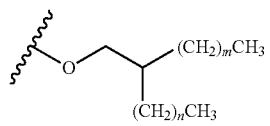<br>$m = 9, n = 7$ |
| 63 | —COOH | H | —COOH | 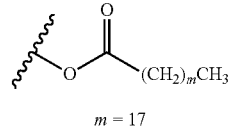<br>$m = 17$ |
| 64 | —COOH | H | —COOH | 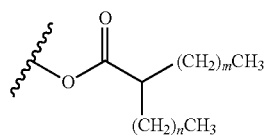<br>$m = 11, n = 9$<br>$m = 7, n = 5$<br>$m = 5, n = 3$ |

TABLE 1-continued
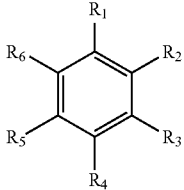
$R_4$ and $R_6$ = H
| | $R_1$ | $R_2$ | $R_3$ | $R_5$ |
|---|---|---|---|---|
| 65 | —COOH | H | —COOH | 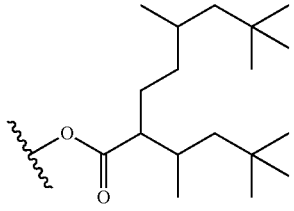 [SMILES: *OC(=O)C(CCC(C)CC(C)(C)C)C(C)CC(C)(C)C] |
| 66 | —CONH$_2$ | H | —CONH$_2$ | 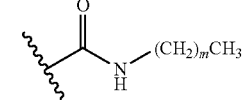<br>$m = 17$ |
| 67 | —CONH$_2$ | H | —CONH$_2$ | 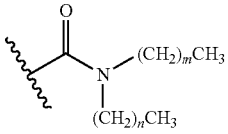<br>$m = 11, n = 9$ |
| 68 | —CONH$_2$ | H | —CONH$_2$ | 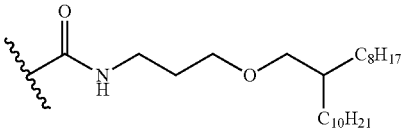 |
| 69 | —CONH$_2$ | H | —CONH$_2$ | 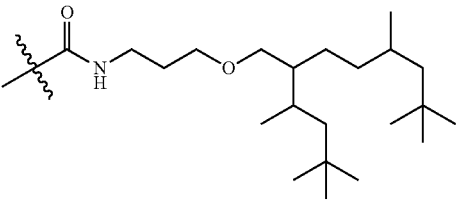 [SMILES: *C(=O)NCCCOCC(CCC(C)CC(C)(C)C)C(C)CC(C)(C)C] |
| 70 | —CONH$_2$ | H | —CONH$_2$ | 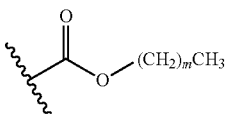<br>$m = 15$ |
| 71 | —CONH$_2$ | H | —CONH$_2$ | 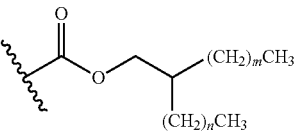<br>$m = 9, n = 7$ |

TABLE 1-continued
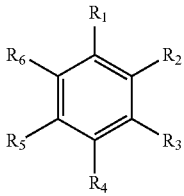
R$_4$ and R$_6$ = H
| | R$_1$ | R$_2$ | R$_3$ | R$_5$ |
|---|---|---|---|---|
| 72 | —CONH$_2$ | H | —CONH$_2$ | 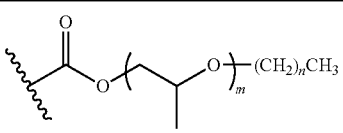<br>$m = 2, n = 3$<br>$m = 3, n = 3$ |
| 73 | —CONH$_2$ | H | —CONH$_2$ | 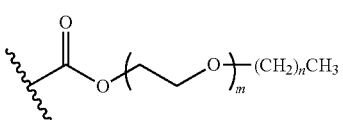<br>$m = 1, n = 3$<br>$m = 2, n = 3$ |
| 74 | —CONH$_2$ | H | —CONH$_2$ | 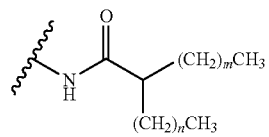<br>$m = 11, n = 9$<br>$m = 7, n = 5$<br>$m = 5, n = 3$ |
| 75 | —CONH$_2$ | H | —CONH$_2$ | 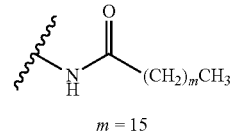<br>$m = 15$ |
| 76 | —CONH$_2$ | H | —CONH$_2$ | 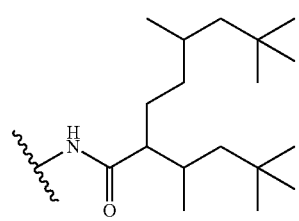 [SMILES: *NC(=O)C(CCC(C)CC(C)(C)C)C(C)CC(C)(C)C] |
| 77 | —CONH$_2$ | H | —CONH$_2$ | 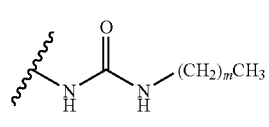<br>$m = 17$ |
| 78 | —CONH$_2$ | H | —CONH$_2$ | 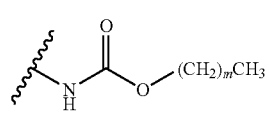<br>$m = 17$ |

TABLE 1-continued
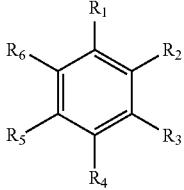
R4 and R6 = H
| | R1 | R2 | R3 | R5 |
|---|---|---|---|---|
| 79 | —CONH$_2$ | H | —CONH$_2$ | 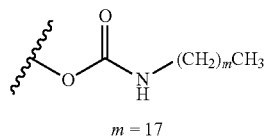<br>$m = 17$ |
| 80 | —CONH$_2$ | H | —CONH$_2$ | 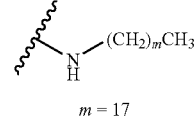<br>$m = 17$ |
| 81 | —CONH$_2$ | H | —CONH$_2$ | 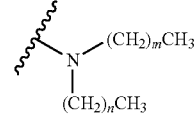<br>$m = 17$ |
| 82 | —CONH$_2$ | H | —CONH$_2$ | 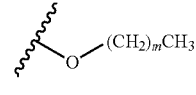<br>$m = 17$ |
| 83 | —CONH$_2$ | H | —CONH$_2$ | 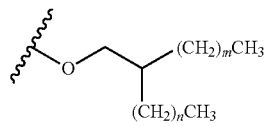<br>$m = 9, n = 7$ |
| 84 | —CONH$_2$ | H | —CONH$_2$ | 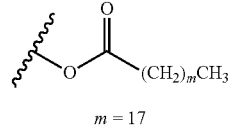<br>$m = 17$ |
| 85 | —CONH$_2$ | H | —CONH$_2$ | 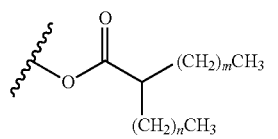<br>$m = 11, n = 9$<br>$m = 7, n = 5$<br>$m = 5, n = 3$ |

TABLE 1-continued
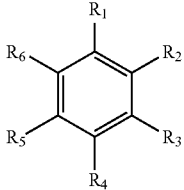
R₄ and R₆ = H
| | R₁ | R₂ | R₃ | R₅ |
|---|---|---|---|---|
| 86 | —CONH₂ | H | —CONH₂ | 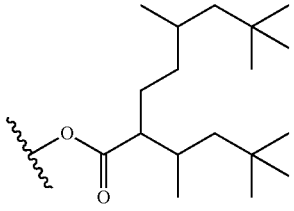 [SMILES: *OC(=O)C(CCC(C)CC(C)(C)C)C(C)CC(C)(C)C] |
| 87 | —COOH | —COOH | H | 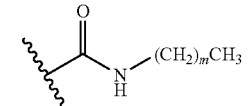<br>$m = 17$ |
| 88 | —COOH | —COOH | H | 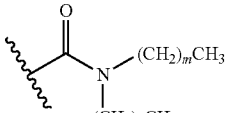<br>$m = 11, n = 9$ |
| 89 | —COOH | —COOH | H | 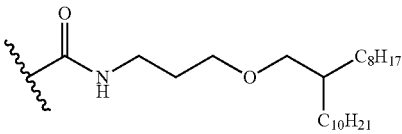 |
| 90 | —COOH | —COOH | H | 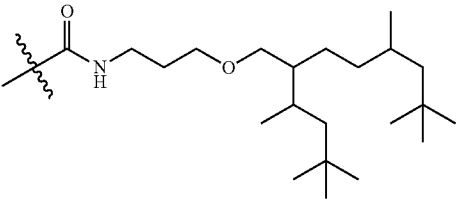 [SMILES: *C(=O)NCCCOCC(CCC(C)CC(C)(C)C)C(C)CC(C)(C)C] |
| 91 | —COOH | —COOH | H | 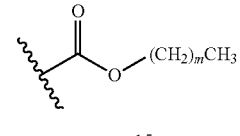<br>$m = 15$ |
| 92 | —COOH | —COOH | H | 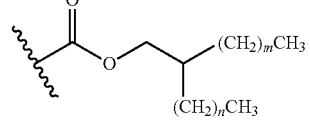<br>$m = 9, n = 7$ |

TABLE 1-continued
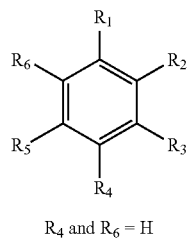
$R_4$ and $R_6$ = H
| | $R_1$ | $R_2$ | $R_3$ | $R_5$ |
|---|---|---|---|---|
| 93 | —COOH | —COOH | H | ![structure] $m = 2, n = 3$; $m = 3, n = 3$ |
| 94 | —COOH | —COOH | H | ![structure] $m = 1, n = 3$; $m = 2, n = 3$ |
| 95 | H | —COOH | ![structure] $m = 17$ | —COOH |
| 96 | H | —COOH | ![structure] $m = 11, n = 9$ | —COOH |
| 97 | H | —COOH | ![structure with $C_8H_{17}$, $C_{10}H_{21}$] | —COOH |
| 98 | H | —COOH | ![structure] | —COOH |
| 99 | H | —COOH | ![structure] $m = 17$ | —COOH |

TABLE 1-continued
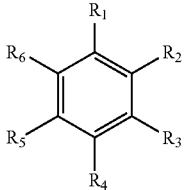
$R_4$ and $R_6$ = H
| | $R_1$ | $R_2$ | $R_3$ | $R_5$ |
|---|---|---|---|---|
| 100 | H | —COOH | 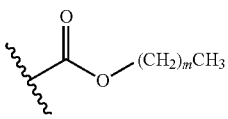<br>$m = 17$ | —COOH |
| 101 | H | —COOH | 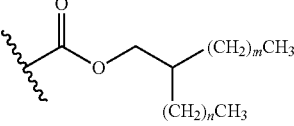<br>$m = 9, n = 7$ | —COOH |
| 102 | H | —COOH | 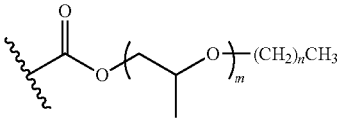<br>$m = 2, n = 3$<br>$m = 3, n = 3$ | —COOH |
| 103 | H | —COOH | 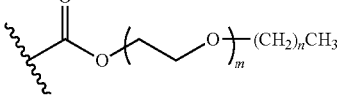<br>$m = 1, n = 3$<br>$m = 2, n = 3$ | —COOH |
| 104 | H | —COOH | 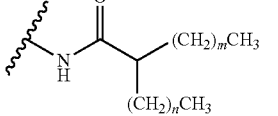<br>$m = 11, n = 9$<br>$m = 7, n = 5$<br>$m = 5, n = 3$ | —COOH |
| 105 | H | —COOH | 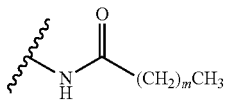<br>$m = 17$ | —COOH |
| 106 | H | —COOH | 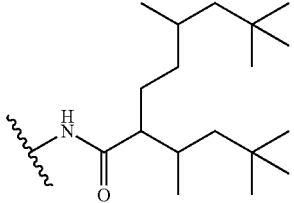 | —COOH |

TABLE 1-continued
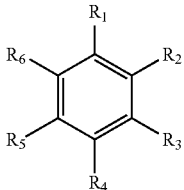
$R_4$ and $R_6$ = H
| | $R_1$ | $R_2$ | $R_3$ | $R_5$ |
|---|---|---|---|---|
| 107 | H | —COOH | 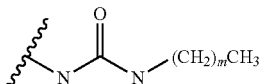<br>$m = 17$ | —COOH |
| 108 | H | —COOH | 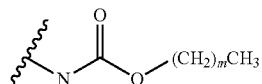<br>$m = 17$ | —COOH |
| 109 | H | —COOH | 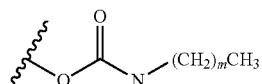<br>$m = 17$ | —COOH |
| 110 | H | —COOH | 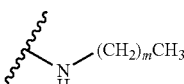<br>$m = 17$ | —COOH |
| 111 | H | —COOH | 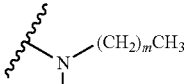<br>$m = 17$ | —COOH |
| 112 | H | —COOH | 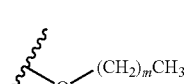<br>$m = 17$ | —COOH |
| 113 | H | —COOH | 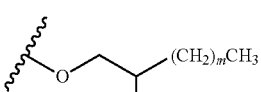<br>$m = 9, n = 7$ | —COOH |
| 114 | H | —COOH | 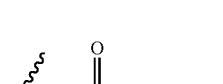<br>$m = 17$ | —COOH |

TABLE 1-continued
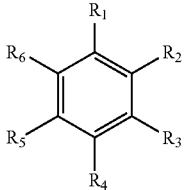
$R_4$ and $R_6$ = H
| | $R_1$ | $R_2$ | $R_3$ | $R_5$ |
|---|---|---|---|---|
| 115 | H | —COOH | 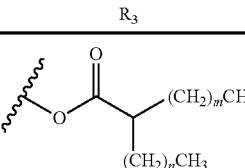<br>$m = 11, n = 9$<br>$m = 7, n = 5$<br>$m = 5, n = 3$ | —COOH |
| 116 | H | —COOH | 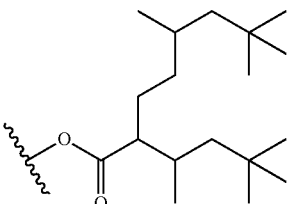 | —COOH |
| 117 | H | —CONH$_2$ | 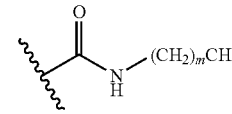<br>$m = 17$ | —CONH$_2$ |
| 118 | H | —CONH$_2$ | 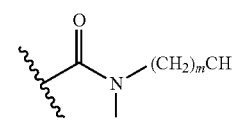<br>$m = 11, n = 9$ | —CONH$_2$ |
| 119 | H | —CONH$_2$ | 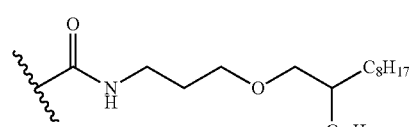 | —CONH$_2$ |
| 120 | H | —CONH$_2$ | 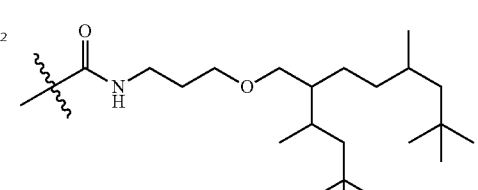 | —CONH$_2$ |
| 121 | H | —CONH$_2$ | 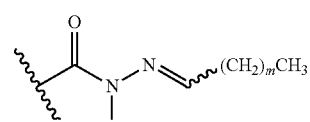<br>$m = 17$ | —CONH$_2$ |

TABLE 1-continued
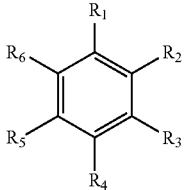
$R_4$ and $R_6$ = H
| | $R_1$ | $R_2$ | $R_3$ | $R_5$ |
|---|---|---|---|---|
| 122 | H | —CONH$_2$ | 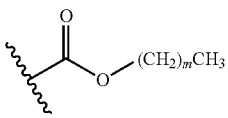<br>m = 17 | —CONH$_2$ |
| 123 | H | —CONH$_2$ | 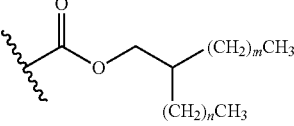<br>m = 9, n = 7 | —CONH$_2$ |
| 124 | H | —CONH$_2$ | 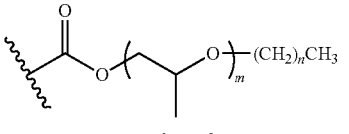<br>m = 2, n = 3<br>m = 3, n = 3 | —CONH$_2$ |
| 125 | H | —CONH$_2$ | 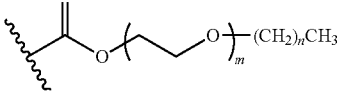<br>m = 1, n = 3<br>m = 2, n = 3 | —CONH$_2$ |
| 126 | H | —CONH$_2$ | 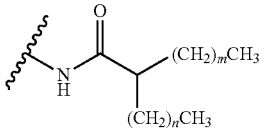<br>m = 11, n = 9<br>m = 7, n = 5<br>m = 5, n = 3 | —CONH$_2$ |
| 127 | H | —CONH$_2$ | 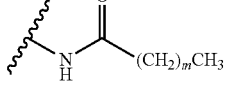<br>m = 17 | —CONH$_2$ |
| 128 | H | —CONH$_2$ | 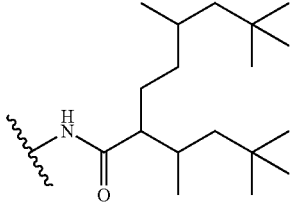 | —CONH$_2$ |

TABLE 1-continued
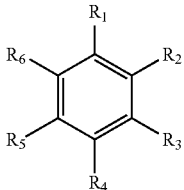
R$_4$ and R$_6$ = H
| | R$_1$ | R$_2$ | R$_3$ | R$_5$ |
|---|---|---|---|---|
| 129 | H | —CONH$_2$ | 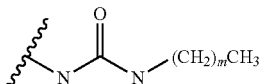<br>m = 17 | —CONH$_2$ |
| 130 | H | —CONH$_2$ | 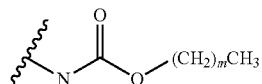<br>m = 17 | —CONH$_2$ |
| 131 | H | —CONH$_2$ | 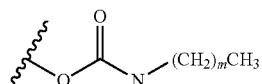<br>m = 17 | —CONH$_2$ |
| 132 | H | —CONH$_2$ | 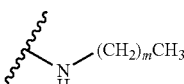<br>m = 17 | —CONH$_2$ |
| 133 | H | —CONH$_2$ | 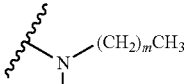<br>m = 17 | —CONH$_2$ |
| 134 | H | —CONH$_2$ | 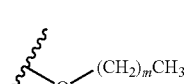<br>m = 17 | —CONH$_2$ |
| 135 | H | —CONH$_2$ | 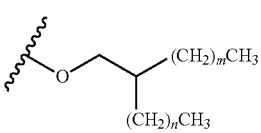<br>m = 9, n = 7 | —CONH$_2$ |
| 136 | H | —CONH$_2$ | 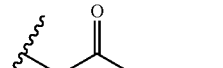<br>m = 17 | —CONH$_2$ |

TABLE 1-continued
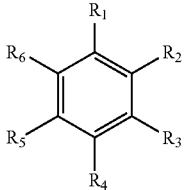
$R_4$ and $R_6$ = H
| | $R_1$ | $R_2$ | $R_3$ | $R_5$ |
|---|---|---|---|---|
| 137 | H | —CONH$_2$ | 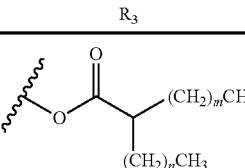<br>$m = 11, n = 9$<br>$m = 7, n = 5$<br>$m = 5, n = 3$ | —CONH$_2$ |
| 138 | H | —CONH$_2$ | 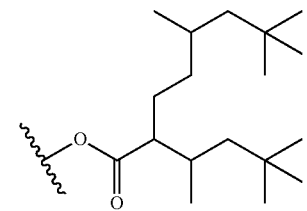 [SMILES: *OC(=O)C(CCC(C)CC(C)(C)C)C(C)CC(C)(C)C] | —CONH$_2$ |
TABLE 2
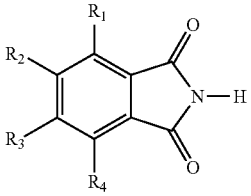
| | $R_1$ | $R_2$ | $R_3$ | $R_4$ |
|---|---|---|---|---|
| 1 | H | H | 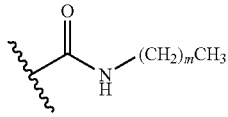<br>$m = 17$ | H |
| 2 | H | H | 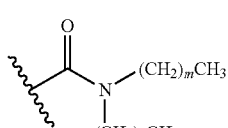<br>$m = 11, n = 9$ | H |
| 3 | H | H | 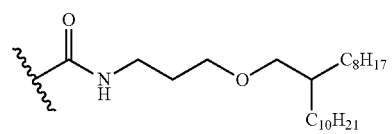 | H |
TABLE 2-continued
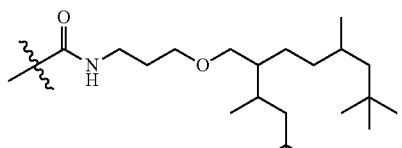
| | $R_1$ | $R_2$ | $R_3$ | $R_4$ |
|---|---|---|---|---|
| 4 | H | H | 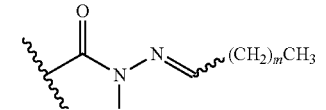 | H |
| 5 | H | H | 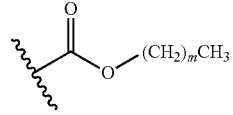<br>$m = 17$ | H |
| 6 | H | H | <br>$m = 17$ | H |

TABLE 2-continued
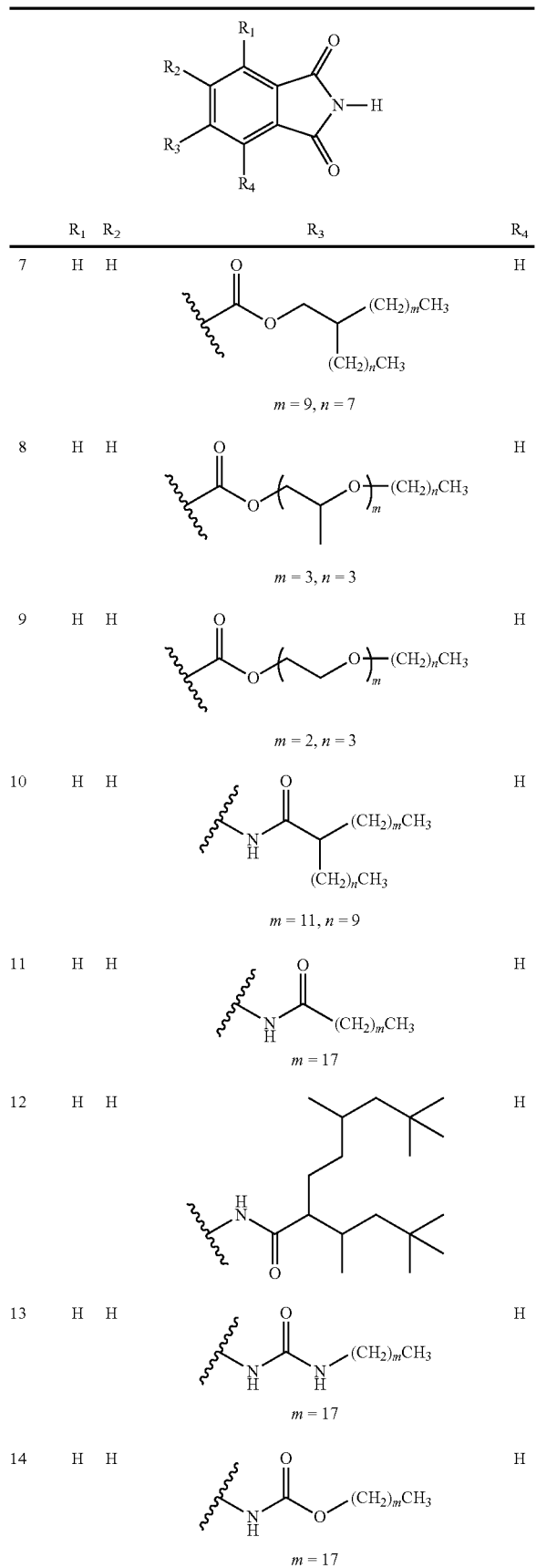
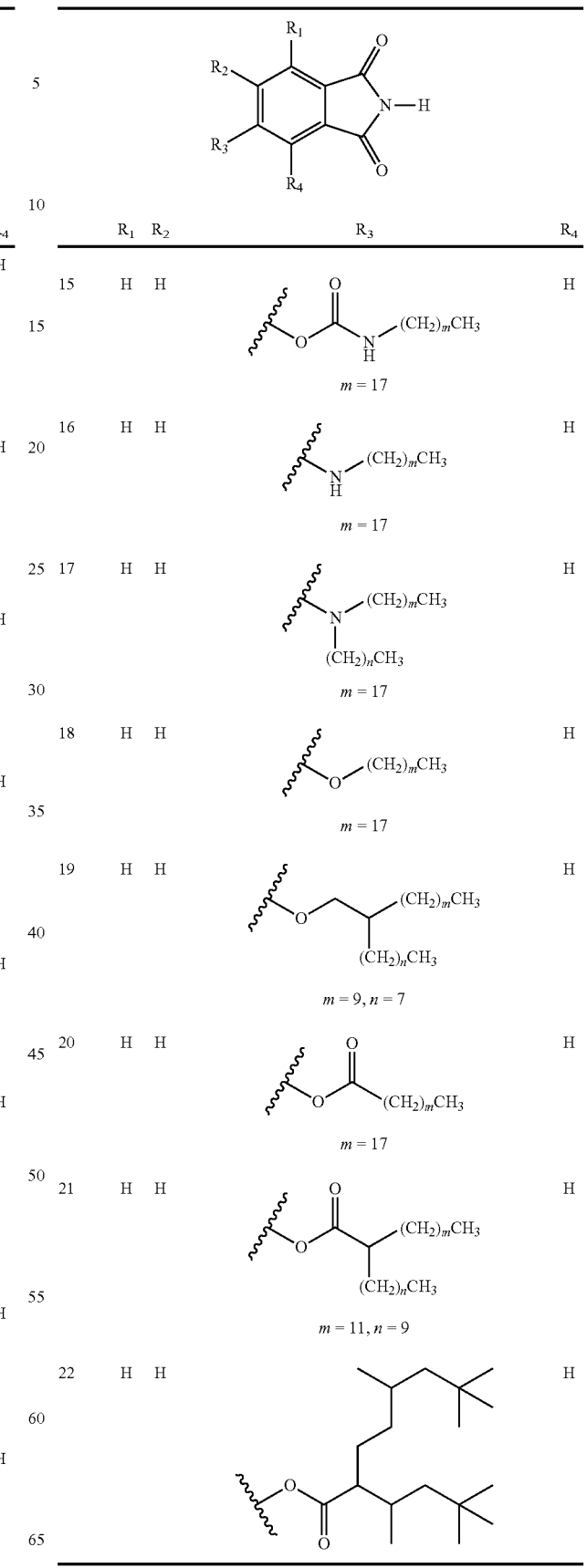

TABLE 3

| | $R_y$ | | $R_1$ | $R_2$ | $R_3$ | $R_4$ | $R_5$ |
|---|---|---|---|---|---|---|---|
| 1 | (structure shown) | X = NH | H | —COOH | H | —COOH | H |
| 2 | (structure shown) | X = O | H | —COOH | H | —COOH | H |

TABLE 3-continued
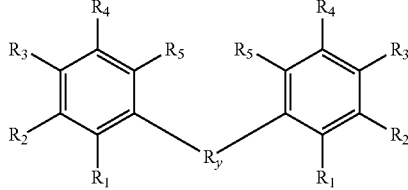
| | $R_y$ | | $R_1$ | $R_2$ | $R_3$ | $R_4$ | $R_5$ |
|---|---|---|---|---|---|---|---|
| 3 |  | X = NH | H | —COOH | H | —COOH | H |
| 4 | 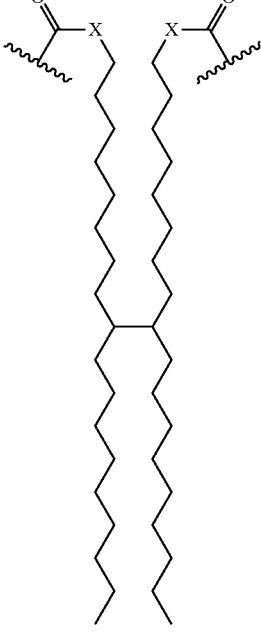 | X = O | H | —COOH | H | —COOH | H |

TABLE 3-continued
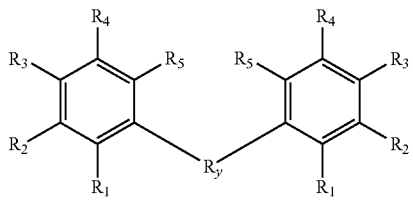
| | $R_y$ | | $R_1$ | $R_2$ | $R_3$ | $R_4$ | $R_5$ |
|---|---|---|---|---|---|---|---|
| 5 |  | $X_1 =$<br>$X_2 = NH$ | H | —COOH | H | —COOH | H |
| 6 | 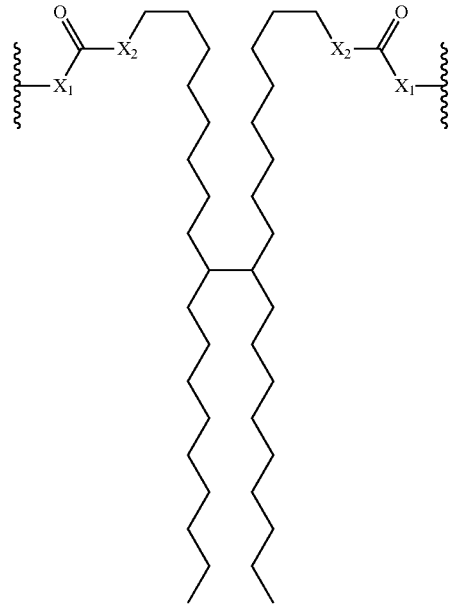 | $X_1 = O$,<br>$X_2 = NH$ | H | —COOH | H | —COOH | H |

TABLE 3-continued
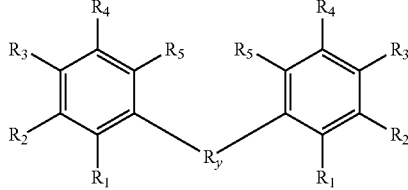
| | $R_y$ | | $R_1$ | $R_2$ | $R_3$ | $R_4$ | $R_5$ |
|---|---|---|---|---|---|---|---|
| 7 |  | | X = NH | H | —CONH$_2$ | H | —CONH$_2$ | H |
| 8 | 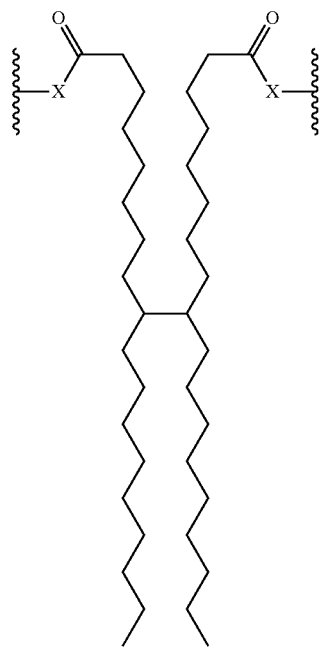 | | X = O | H | —CONH$_2$ | H | —CONH$_2$ | H |

TABLE 3-continued
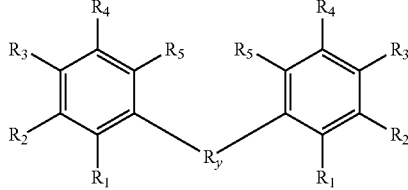
| | $R_y$ | $R_1$ | $R_2$ | $R_3$ | $R_4$ | $R_5$ |
|---|---|---|---|---|---|---|
| 9 |  | X = NH | H | —CONH$_2$ | H | —CONH$_2$ | H |
| 10 | 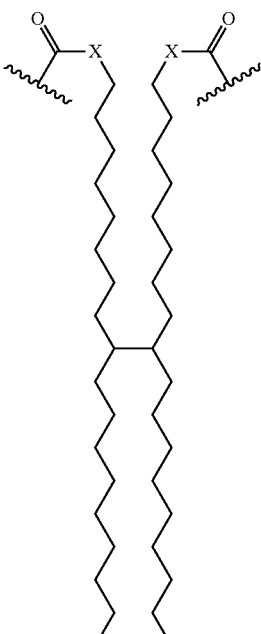 | X = O | H | —CONH$_2$ | H | —CONH$_2$ | H |

TABLE 3-continued
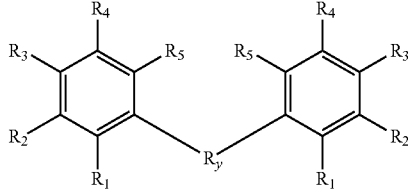
| $R_y$ | | $R_1$ | $R_2$ | $R_3$ | $R_4$ | $R_5$ |
|---|---|---|---|---|---|---|
| 11  | $X_1 =$ <br> $X_2 = NH$ | H | —CONH$_2$ | H | —CONH$_2$ | H |
| 12 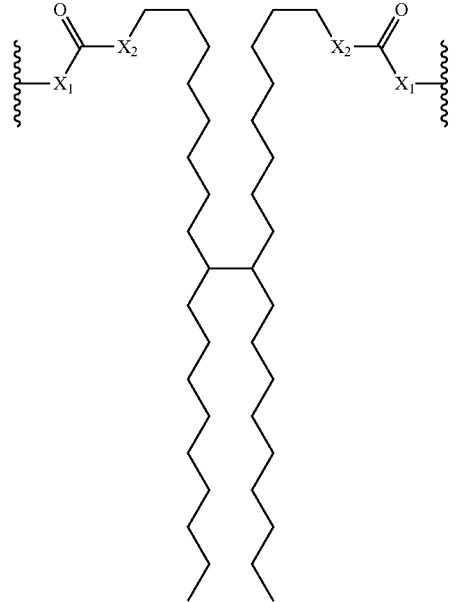 | $X_1 = O,$ <br> $X_2 = NH$ | H | —CONH$_2$ | H | —CONH$_2$ | H |

TABLE 3-continued
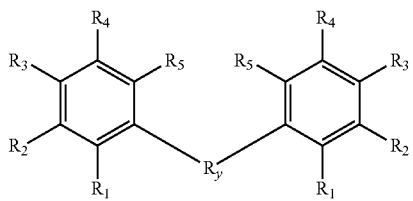
| | $R_y$ | | $R_1$ | $R_2$ | $R_3$ | $R_4$ | $R_5$ |
|---|---|---|---|---|---|---|---|
| 13 |  | X = NH | H | —COOH | —COOH | H | H |
| 14 | 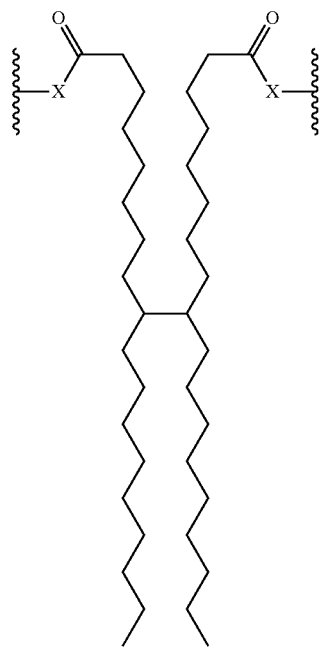 | X = O | H | —COOH | —COOH | H | H |

TABLE 3-continued
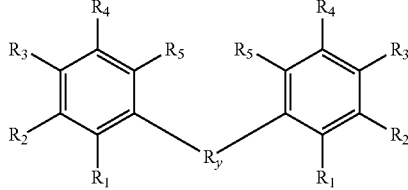
| | $R_y$ | | $R_1$ | $R_2$ | $R_3$ | $R_4$ | $R_5$ |
|---|---|---|---|---|---|---|---|
| 15 | 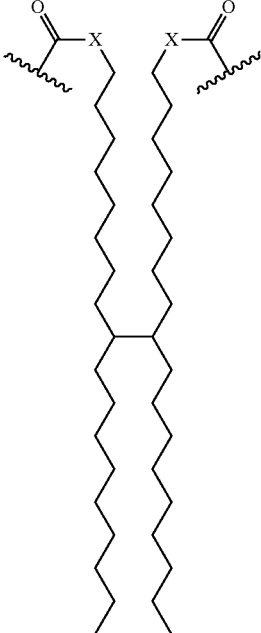 | X = NH | H | —COOH | —COOH | H | H |
| 16 | 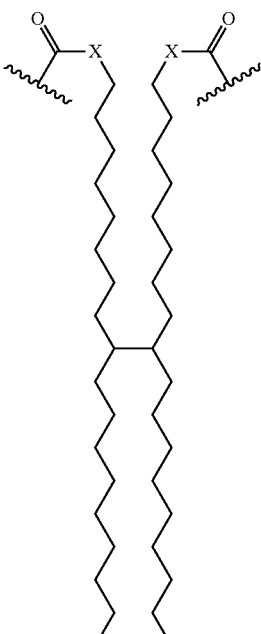 | X = O | H | —COOH | —COOH | H | H |

TABLE 3-continued

| | $R_y$ | $R_1$ | $R_2$ | $R_3$ | $R_4$ | $R_5$ |
|---|---|---|---|---|---|---|
| 17 | $X_1 =$ $X_2 = NH$ | H | —COOH | —COOH | H | H |
| 18 | $X_1 = O,$ $X_2 = NH$ | H | —COOH | —COOH | H | H |

TABLE 3-continued
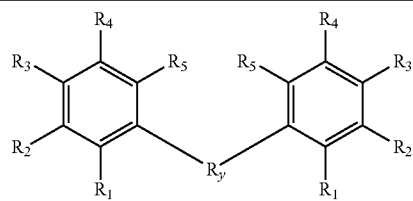
| | $R_y$ | | $R_1$ | $R_2$ | $R_3$ | $R_4$ | $R_5$ |
|---|---|---|---|---|---|---|---|
| 19 | | X = NH | H | H | —COOH | H | H |
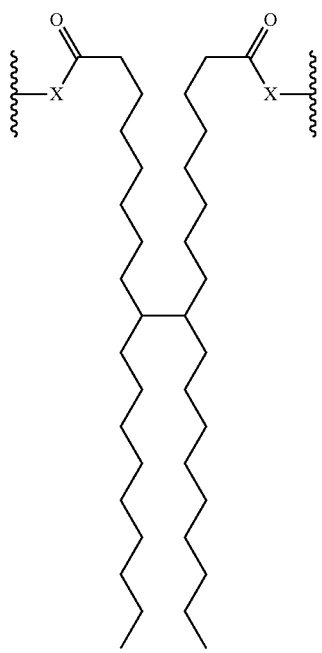
| 20 | | X = O | H | H | —COOH | H | H |
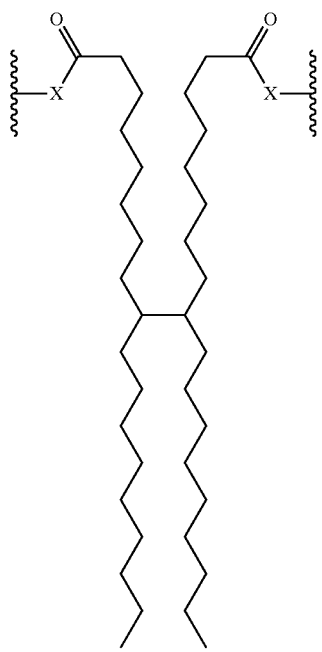

TABLE 3-continued
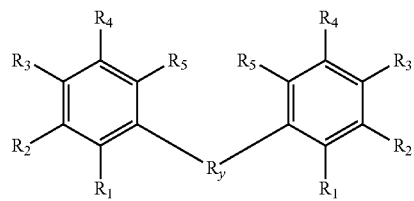
| R$_y$ | | R$_1$ | R$_2$ | R$_3$ | R$_4$ | R$_5$ |
|---|---|---|---|---|---|---|
| 21 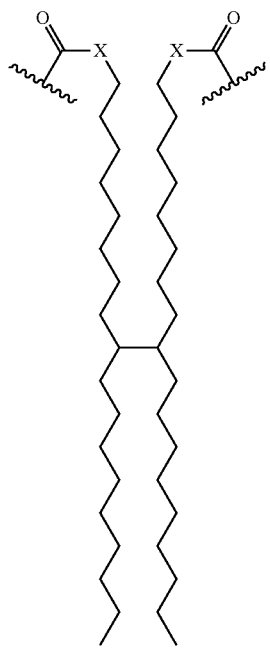 | X = NH | H | H | —COOH | H | H |
| 22 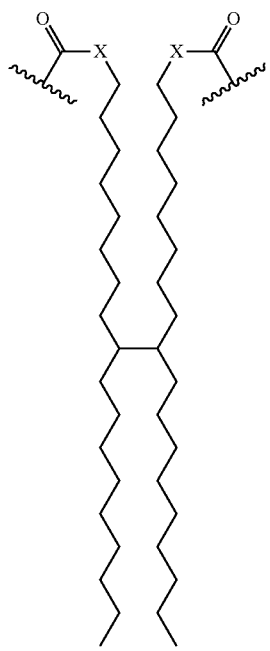 | X = O | H | H | —COOH | H | H |

TABLE 3-continued

| $R_y$ | | $R_1$ | $R_2$ | $R_3$ | $R_4$ | $R_5$ |
|---|---|---|---|---|---|---|
| 23 | $X_1 =$ <br> $X_2 = NH$ | H | H | —COOH | H | H |
| 24 | $X_1 = O$, <br> $X_2 = NH$ | H | H | —COOH | H | H |

TABLE 3-continued
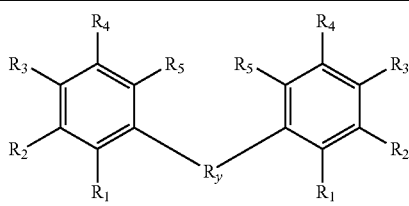
| | $R_y$ | $R_1$ | $R_2$ | $R_3$ | $R_4$ | $R_5$ |
|---|---|---|---|---|---|---|
| 25 |  | X = NH | H | H | —CONH$_2$ | H | H |
| 26 | 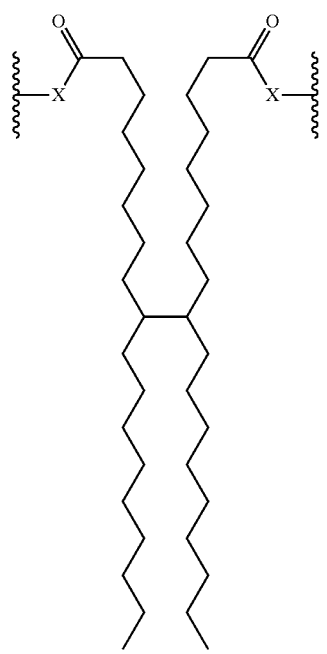 | X = O | H | H | —CONH$_2$ | H | H |

TABLE 3-continued
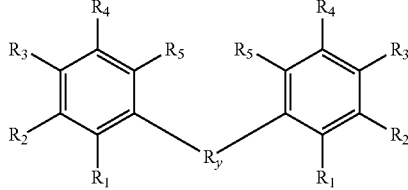
| | $R_y$ | $R_1$ | $R_2$ | $R_3$ | $R_4$ | $R_5$ |
|---|---|---|---|---|---|---|
| 27 |  | X = NH | H | H | —CONH$_2$ | H | H |
| 28 | 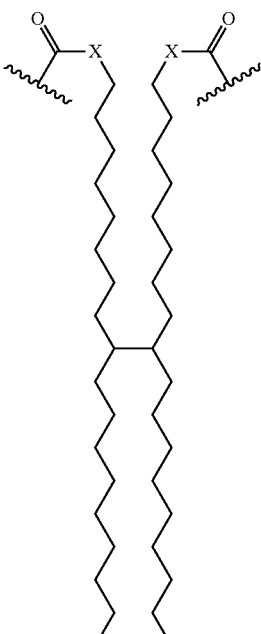 | X = O | H | H | —CONH$_2$ | H | H |

TABLE 3-continued
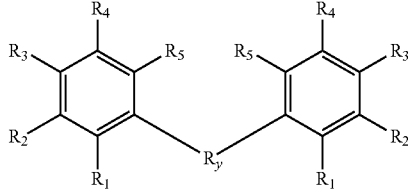
| | R$_y$ | R$_1$ | R$_2$ | R$_3$ | R$_4$ | R$_5$ |
|---|---|---|---|---|---|---|
| 29 | X$_1$ = <br>X$_2$ = NH | H | H | —CONH$_2$ | H | H |
| 30 | X$_1$ = O,<br>X$_2$ = NH 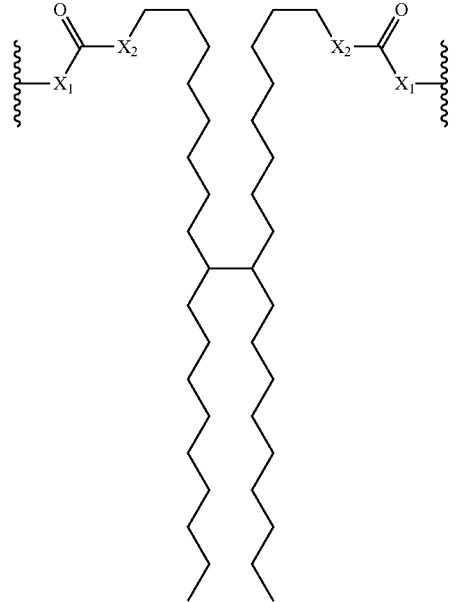 | H | H | —CONH$_2$ | H | H |

TABLE 3-continued
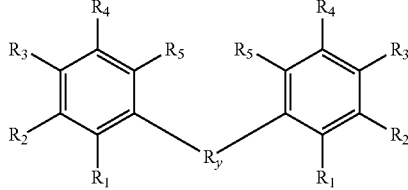
| | $R_y$ | | $R_1$ | $R_2$ | $R_3$ | $R_4$ | $R_5$ |
|---|---|---|---|---|---|---|---|
| 31 | 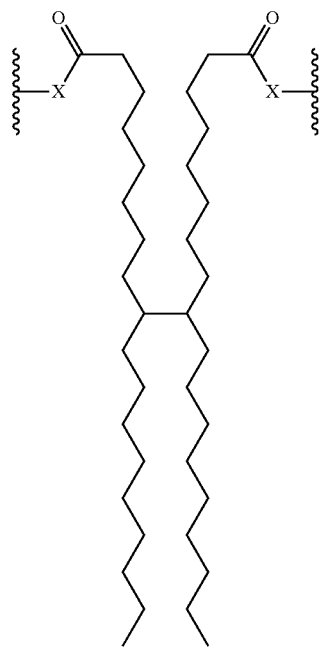 | X = NH | —COOH | H | H | —COOH | H |
| 32 | 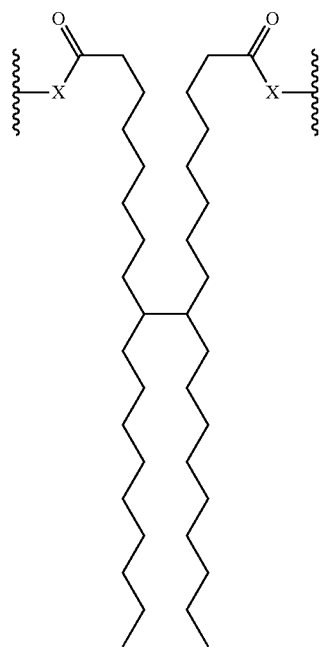 | X = O | —COOH | H | H | —COOH | H |

TABLE 3-continued
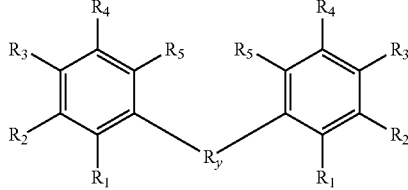
| | $R_y$ | | $R_1$ | $R_2$ | $R_3$ | $R_4$ | $R_5$ |
|---|---|---|---|---|---|---|---|
| 33 | 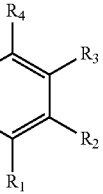 | X = NH | —COOH | H | H | —COOH | H |
| 34 | 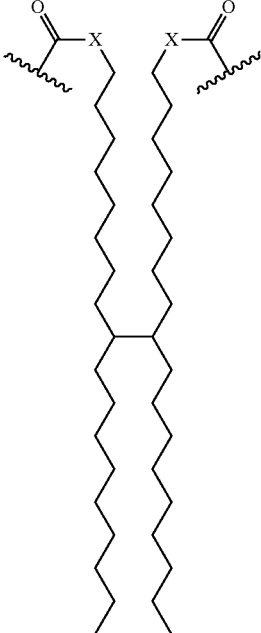 | X = O | —COOH | H | H | —COOH | H |

TABLE 3-continued

| $R_y$ | | $R_1$ | $R_2$ | $R_3$ | $R_4$ | $R_5$ |
|---|---|---|---|---|---|---|
| 35 | $X_1$ = <br> $X_2$ = NH | —COOH | H | H | —COOH | H |
| 36 | $X_1$ = <br> $X_2$ = NH | —COOH | H | H | —COOH | H |

TABLE 3-continued
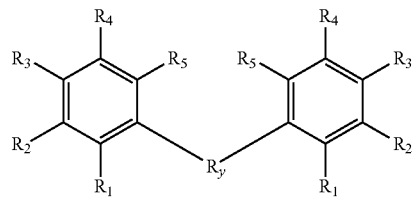
| R_y | | R_1 | R_2 | R_3 | R_4 | R_5 |
|---|---|---|---|---|---|---|
| 37 | | X = NH —CONH$_2$ | H | H | —CONH$_2$ | H |
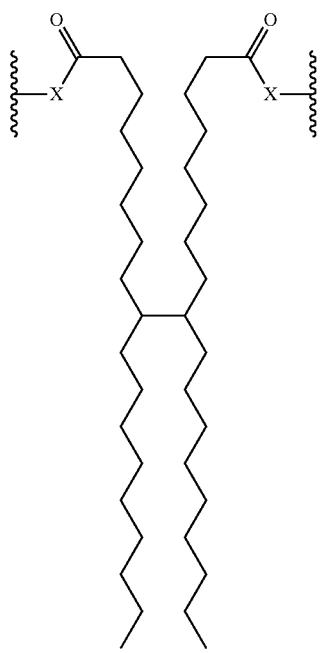
| 38 | | X = O —CONH$_2$ | H | H | —CONH$_2$ | H |
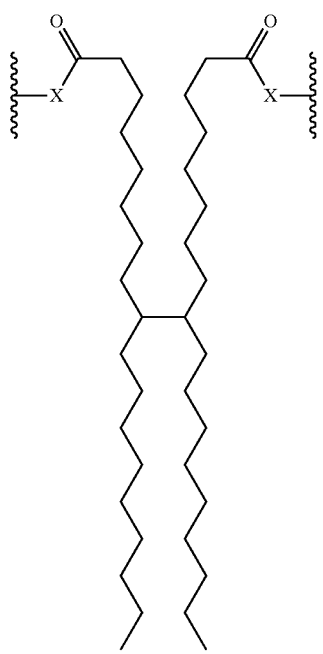

TABLE 3-continued
| $R_y$ | | $R_1$ | $R_2$ | $R_3$ | $R_4$ | $R_5$ |
|---|---|---|---|---|---|---|
| 39 | | X = NH | —CONH$_2$ | H | H | —CONH$_2$ | H |
| 40 | | X = O | —CONH$_2$ | H | H | —CONH$_2$ | H |
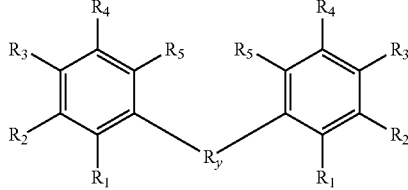

TABLE 3-continued

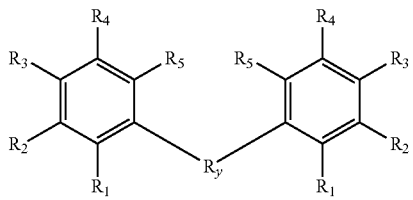

| | $R_y$ | | $R_1$ | $R_2$ | $R_3$ | $R_4$ | $R_5$ |
|---|---|---|---|---|---|---|---|
| 41 | 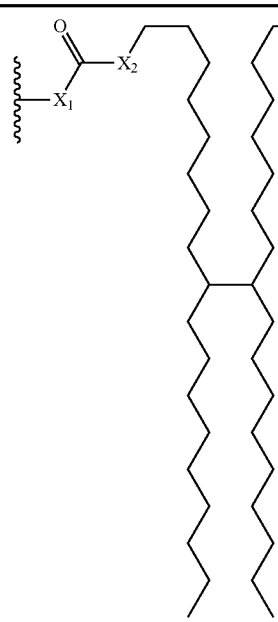 | $X_1=$ —CONH$_2$<br>$X_2=$ NH | | H | H | —CONH$_2$ | H |
| 42 |  | $X_1=$ O,<br>$X_2=$ NH | —CONH$_2$ | H | H | —CONH$_2$ | H |

Alkyl amides of aromatic acids, such as in the [(benzene)-(C═O)NH—R] moiety, can be prepared from commercially available materials using any desired or effective method. For example, an aromatic acid chloride can be reacted with a suitable alkylamine in approximately equimolar amounts at a suitable temperature, optionally in the presence of a solvent, and optionally in the presence of a base.

Alkyl amides of aromatic acids, such as in [(benzene)-(C═O)NH—R] moiety, can be prepared from commercially available materials using any desired or effective method. For example, an amino aromatic acid ester can be reacted with a suitable alkanoic acid chloride in approximately equimolar amounts at a suitable temperature, optionally in the presence of a solvent, and optionally in the presence of a base, followed by hydrolysis of the ester groups.

There are many methods for activating aromatic and alkanoic acids for reactivity with nucleophiles such as amines, alcohols, and the like, that are well-known and familiar to those skilled in the art. One method involves conversion of the aromatic or alkanoic acid to the corresponding aromatic or alkanoic acid chloride, respectively, using any desired or effective method to those skilled in the art. For example, the aromatic or alkanoic acid chloride may be prepared from the corresponding aromatic or alkanoic acid precursor, respectively, by reaction with a chlorinating reagent, typically in the presence of a solvent, and optionally in the presence of a catalyst. Suitable chlorinating reagents may include, but are not limited, to oxalyl chloride, thionyl chloride, phosphorous trichloride, or phosphorous pentachloride. Other reagents may also be used to activate the carboxylic acid for reaction with the amine, including but not limited to dicyclohexylcarbodiimide (DCC), diisopropylcarbodiimide (DIC), and benzotriazoles.

More specifically, the aromatic or alkanoic acid can be reacted with oxalyl chloride in the presence of an optional catalyst at about 0 to about 5° C. in a suitable solvent. Examples of catalysts include N,N-dimethylformamide (DMF). The catalyst, when used, can be present in any desired or effective amount. In one embodiment at least about 0.1 mol percent, in another embodiment at least about 0.5 mol percent, in another embodiment at least about 1 mol percent, in another embodiment at least about 10 mol %, and yet in another embodiment at least about 20 mol % based on the amount of oxalyl chloride, although the amount can be outside these ranges.

The aromatic or alkanoic acid and oxalyl chloride are present in any desired or effective relative amounts, such as about 0.8 mol to about 3.0 mol of oxalyl chloride per every mol of aromatic or alkanoic acid, or about 1.0 mol to about 2.0 mol of oxalyl chloride per every mol of aromatic or alkanoic acid, or about 1.2 mol to about 1.5 mol of oxalyl chloride per every mol of aromatic or alkanoic acid, although the relative amounts can be outside of these ranges.

Subsequent to the reaction between the aromatic acid or alkanoic acid and oxalyl chloride, the first reaction product need not be recovered; the reaction mixture can be appropriately mixed with a suitable amine, along with the addition of solvent and base if desired, to complete the reaction. Alternatively, the first reaction product acid chloride may be isolated prior to mixing with the amine, along with the addition of an optional solvent and base if desired to complete the reaction. The first reaction product and the amine can be present in any desired or effective relative amounts, such as about 0.8 mol to about 1.1 mol, or about 1.0 mol, of the first reaction product per every amino group, although the relative amounts can be outside of these ranges.

The reactions to form the alkylated amides of aromatic acid ester compounds may be carried out in an anhydrous solvent such as tetrahydrofuran or dichloromethane in the presence of a hindered base such as a triethylamine or tertiary alkylamine, 2,2,6,6-tetramethylpiperidine, or 2,6-dimethylpyridine and the like. The alkanoyl or alkylamido aromatic acid esters may then be converted to their corresponding acids by reaction with at least an equimolar amount of a suitable hydroxide base such as sodium, potassium, lithium, or cesium hydroxide at a suitable temperature, and optionally in the presence of a polar solvent such as water, methanol, ethanol, isopropanol, and the like or mixtures of water:methanol, water:ethanol, water:isopropanol, and the like.

Aromatic acids that are derivatized with sterically bulky ester groups, such as in [(arene)-(C═O)—OR] moiety, are prepared for example by reacting a suitable aromatic acid chloride with about 0.5 to about 3.0 equivalents per acid chloride group of an appropriate sterically bulky aliphatic alcohol in a suitable anhydrous solvent, such as tetrahydrofuran or dichloromethane in the presence of a hindered base such as a triethylamine or tertiary alkylamine, 2,2,6,6-tetramethylpiperidine, or 2,6-dimethylpyridine and the like. Quenching the reaction with an excess of water at any point during the reaction converts any unreacted acid chloride groups to the corresponding carboxylic acid groups.

N-Alkylated ureidoaromatic acid esters can be prepared by conventional methods from alkylisocyanate reactants by any desired or effective method. For example, a desired aminoaromatic acid ester (e.g., 1,3-dimethyl-5-aminoisophthalate) can be reacted with a desired alkylisocyanate of the formula OCN—$R_1$ in approximately equimolar amounts per amine group at a specified temperature, optionally in the presence of a solvent. Thereafter the resulting product is obtained in very high purity simply by precipitation with water, followed by washing and drying.

The alkylisocyanate and amino aromatic acid ester can be present in any desired or effective relative amounts, such as in one embodiment about 0.4 mol to about 1.4 mol, or about 0.6 mol to about 1.2 mol, or about 0.8 mol to about 1.0 mol of the first reaction product per amine group of the amino aromatic acid ester, although the relative amounts can be outside of these ranges.

O-Alkylated carbamates or urethane aromatic acid ester derivatives, can be prepared readily by reaction of a desired hydroxy aromatic acid ester, respectively, with an alkyl isocyanate, such as octadecyl isocyanate or the diisocyanate derivative of C-36 dimer acid (obtained from Henkel Corp. as DDI 1410™), respectively, in the presence of a catalytic amount of a Lewis Acid catalyst, such as for example dibutyltin dilaurate, and with mild heating.

The alkylisocyanate and hydroxy aromatic acid ester can be present in any desired or effective relative amounts, such as about 0.4 mol to about 1.4 mol or about 0.6 or about 0.8 to about 1.0 or about 1.2 mol of the first reaction product per every hydroxy group of the hydroxy aromatic acid ester, although the relative amounts can be outside of these ranges.

Examples of suitable catalysts include (but are not limited to) Lewis acid catalysts such as dibutyl tin dilaurate, bismuth tris-neodecanoate, cobalt benzoate, lithium acetate, stannous octoate, triethylamine, ferric chloride, aluminum trichloride, boron trichloride, boron trifluoride, titanium tetrachloride, tin tetrachloride, and the like. The catalyst, when present, can be present in any desired or effective amount, such as at least about 0.2 mole percent, at least about 0.5 mole percent, or at least about 1.0 mole percent, but desirably no more than about 10 mole percent, or no more than about 7.5 mole percent, or no more than about 5.0 mole percent, based on the amount of isocyanate, although the amount can be outside these ranges.

Alkoxy aromatic acid derivatives are prepared by an alkyl substitution (or, alkylation) reaction of a hydroxy aromatic acid methyl ester, with a suitable sterically bulky alkylating reagent. Examples of such sterically bulky alkylating reagents include, for example, secondary alkyl halides, wherein the halogen is selected from F, Cl, Br, I; or the suitable alkyl ester of an alkanesulfonate or arenesulfonate reagent such as alkyl methanesulfonates (commonly known as alkyl mesylates, or alkyl para-toluenesulfonates (commonly known as alkyl tosylates), or alkyl trifluoromethanesulfonate (commonly known as alkyl triflates) wherein the corresponding leaving group is the mesylate, tosylate or triflate anion; or a suitable alkyl ester of a carboxylic acid, such as alkyl acetate, alkyl formate, alkyl propionate and the like, wherein the leaving group that is displaced is the acetate, formate, propionate, etc. A suitable polar aprotic solvent for such substitution reactions include N,N-dimethylformamide, N,N-dimethylacetamide, N-methyl-2-pyrrolidinone, dimethylsulfoxide, sulfolane, acetone, methyl ethyl ketone, tetrahydrofuran, dimethoxyethane, and other such polar aprotic solvents. Alkylation reactions are conducted in the presence of a mild base such as sodium or potassium carbonate, and at temperatures such as from about 0° C. to about 120° C., or preferably from about 25° C. to about 100° C., depending on the extent of alkylation desired, the leaving group of the alkylating agent, and the reaction solvent employed, although the reaction temperatures can also be outside of the above ranges. Catalysts may optionally be used to speed up the rate of substitution reaction, and suitable catalysts include halide salts such as potassium iodide or sodium iodide, and the like. Following the alkylation reaction, the methyl ester groups are converted to the corresponding free carboxylic acid groups by reaction with sodium or potassium hydroxide in warm methanol.

Analogous benzamides and isophthalamides are subsequently prepared from the corresponding carboxylic acids by first conversion to their acid chloride group using standard procedures described earlier, following by quenching with concentrated ammonia/ammonium hydroxide.

The ester and amide derivatives of phthalic acids containing the sterically bulky aliphatic groups are prepared by reacting commercially available trimellitic anhydride acid chloride with a suitable sterically bulky alkylamine or alkanol in a suitable anhydrous solvent such as tetrahydrofuran or dichloromethane in the presence of hindered base such as triethylamine. The anhydride can be subsequently converted to the resulting phthalic acid group by hydrolysis, for example, with either sodium or potassium hydroxide in methanol.

The types of non-covalent chemical bonding that can occur between separate molecules of the alkylated derivatives of aromatic acids, or between the alkylated derivatives of aromatic acids and other compounds, are, for example, van der Waals forces, ionic or coordination bonding, H-bonding, and/or aromatic pi-stacking bonding. In embodiments, the non-covalent bonding is predominately H-bonding and van der Waals' forces, but can include aromatic pi-stacking bonding as additional or alternative types of non-covalent bonding between the respective molecules.

The organic nanostructures from the alkylated derivatives of aromatic acids described herein can be prepared, for example, by homogeneously mixing a self-assembling, alkylated derivative of aromatic acid having the above formula with a polar or nonpolar liquid under conditions sufficient to effect the extent of dissolution and self-assembly, usually by heating followed by subsequent cooling and aging for a given period of time to allow the desired nanostructures to fully mature. Mixing of the components may be conducted at temperatures ranging between room temperature and the boiling point of the liquid. The self-assembling, alkylated derivative of aromatic acid may be added in the form of powder particles, which may completely dissolve in the liquid to form a clear solution or may only partially dissolve to form a dispersion. Alternatively the self-assembling, alkylated derivative of aromatic acid may be added as a solution dissolved in a suitable solvent including both polar and nonpolar liquids. This liquid that the alkylated derivative of aromatic acid is dissolved in may be the same as the liquid it is being added to, or may be a different liquid. In addition, the liquid to which the solution of alkylated derivative of aromatic acid is being added to may be a good or poor solvent for the alkylated compound and resulting self-assembled nanostructures. The nanostructure compositions of the present disclosure may also be formed, for example, at elevated temperatures by dissolving or dispersing the self-assembling alkylated derivative of aromatic acid in the liquid at elevated temperatures, and thereafter cooling the resulting solution to a lower temperature, whereby a colloid solution or dispersion of nanostructured aggregates forms while aging for a suitable period of time.

According to the present disclosure, the self-assembling alkylated derivatives of aromatic acids may be present in a wide range. An exemplary range is a range of about 0.05% to 20% by weight based upon the liquid of the composition, such as 0.075 to 10%, or 0.1 to 1.5 to 2.0%. The properties of the compositions containing the nanostructures may be controlled depending on the kind and amount of alkylated derivatives of aromatic acids added. A suitable amount of alkylated derivatives of aromatic acids may be readily determined by routine experimentation and will vary with the desired physical property of the composition and other components therein. As is understood by those skilled in the art, a lower amount of alkylated compound often makes the compositions more desirable, inasmuch as the non-assembled, individual alkylated molecules may often demonstrate chemical and physical properties that are different from the end use properties of the compositions containing self-assembled nanostructures from alkylated derivatives of aromatic acids.

More than one species of self-assembling alkylated derivative of aromatic acid may be utilized to form nanostructures in a particular liquid. For example, a mixture of two different isomers or homologues of a particular alkylated derivative of aromatic acid (e.g., different linkages, organic substituents, etc.) may be used.

When preparing the self-assembled nanostructures in accordance with the process of this disclosure, the requisite amount of alkylated derivatives of aromatic acids is mixed with the liquid and the materials are blended, for example under ambient conditions of temperature and pressure. Different temperatures and pressures may be utilized in the mixing process where, for example, loss of vapors, in the case of a low-boiling liquid hydrocarbon, is to be avoided (use lower temperatures and/or higher pressures) or when easier mixing, in the case of higher-boiling liquids, is to be obtained (use higher temperatures and/or lower pressures).

The components may be mixed by any means such as stirring, shaking, or passing the mixtures through a homogenizer, or subjecting to ultrasonic waves to produce a homogeneous composition. Regardless of the method of blending, self-assembled nanostructures are produced as a result of obtaining a solution or dispersion of the alkylated derivatives of aromatic acids in the liquid.

The compositions of self-assembled nanostructures of the present disclosure, once formed, may be contained in liquid or in solid form upon evaporation of the liquid. Liquid compositions may vary, and consist of clear or turbid colloidal solutions, opaque dispersions, settled precipitates, clear viscous (supramolecular)polymer solutions, or thick gels. The viscosity of liquid compositions of the nanostructures varies from thin, pourable type to a shape retaining material (i.e., a gel). The resulting nanostructures may be robust, individually dispersed, or highly cohesive, and are stable in storage for variable periods (depending on the alkylated derivative of aromatic acid, its concentration, the liquid, and the temperature of storage), thermally reversible, and are sheer stress thinnable.

The self-assembled nanostructures made from the alkylated derivatives of aromatic acids described herein generally comprise the alkylated compounds in a major, predominant, substantial, or entire amount of the solid form of the nanostructure. That is, in embodiments, the solid portion of the nanostructures (not including any solvent or liquid carrier that may be included) comprises, consists essentially of, or consists of the alkylated derivatives of aromatic acids. Of course, two or more different alkylated derivatives of aromatic acids can be included, as desired. Thus, in embodiments, the nanostructures do not contain other hydrogen-bonding materials such as steric stabilizers, and do not correspond to nanoparticles that may be formed by association of the alkylated derivatives of aromatic acids with pigment particles.

However, in other embodiments, the nanostructure may comprise one or more additives, such as to provide desired properties to the nanostructure. For example, the additives may provide such properties as hardness, rigidity, porosity, color, or the like to the nanostructure. Such additives in embodiments do not hydrogen bond to the alkylated derivatives of aromatic acids in the nanostructure. Instead, in these embodiments, the additives can be covalently or ionically bound to the nanostructure, or they can be mixed, dispersed, or the like in the nanostructure.

A number of characterization methods are useful for detecting and characterizing self-assembled nanostructures from alkylated derivatives of aromatic acids. The simplest test is to observe any changes in viscosity (rheology) of the liquid containing the alkylated compound relative to the neat liquid alone. A highly viscous fluid or jelly-like material strongly suggests the formation of nanostructured supramolecular aggregates (i.e., supramolecular polymers or gels). If the mixture does not flow under the influence of gravity upon inversion of the sample vial, then the mixture is considered to be a gel. The increase in viscosity and gelation of liquids is known to occur due to the presence and entanglement of long, 1D aggregates.

Microscopy techniques such as optical light microscopy, scanning electron microscopy (SEM), transmission electron microscopy (TEM), atomic force microscopy (AFM)/scanning probe microscopy (SPM), and fluorescence microscopy are useful for determining the size and morphology of the nano (and micro) structures formed from alkylated derivatives of aromatic acids. Samples are typically prepared by depositing a drop of the liquid composition containing the nanostructures onto an appropriate sample substrate such as a carbon film coated copper mesh TEM grid, removing the excess liquid by blotting with filter paper, and then allowing to dry prior to analysis. Dynamic light scattering is also useful for detecting the presence of particles between 1 nm and 1 μm in size, measuring the size/size distribution of the dispersed particles. Rheometry is useful for determining the viscoelastic properties and thermal phase transitions for compositions of the self-assembled nanostructures. X-ray diffraction is useful for characterizing the structure of the self-assembled nanostructures size as phase identification, crystallinity, phase transitions, crystal structure refinement and determination, and size and strain broadening of crystallite nanostructures. NMR spectroscopy is useful in detecting the formation intermolecular noncovalent interactions stabilizing the nanostructures, their diffusion properties, as well as phase transitions. UV-Vis can be used for detecting the presence of nanostructures as well as confirming the presence of intermolecular pi-stacking interactions. FT-IR spectroscopy is also useful for the detection of hydrogen-bonding interactions involved in stabilizing the self-assembled nanostructures. Differential Scanning calorimetry (DSC) is another useful characterization technique, which enables the identification of thermal phase transitions within the compositions containing the nanostructures.

As disclosed in U.S. patent application Ser. No. 12/581,420, the alkylated derivatives of aromatic acids can be used for making nanoscale particles of azo-benzimidazolone organic pigments, by using a bottom-up assembly synthetic approach that makes use of the alkylated derivatives of aromatic acids as amphiphilic surface auxiliaries for controlling the particle size, morphology, dispersion properties and even coloristic properties of the resulting nanopigments. The procedures disclosed therein can be used to make other suitable nanopigments and nanocolorants.

The alkylated derivatives of aromatic acids, and self-assembled structures made from those compounds, can be used in a wide variety of applications. For example, the alkylated derivatives of aromatic acids can be used as organogelators in the formation of organogels, which may then be used as thickening agents for numerous products such as paints, inks, coatings, lubricants, adhesives, personal care products, pharmaceutical and dermatological gels, and even in certain food products, or they can be used in tissue engineering, biomineralization (as templates), catalysis, gel-based scaffolds for energy transfer and light harvesting, and the like. The alkylated derivatives of aromatic acids can also be used in the formation of novel hydrogen bonded liquid crystal materials, where the liquid crystal material can comprise the alkylated derivatives of aromatic acids disclosed herein themselves, or in combination with another complementary H-bonding molecules or polymers with pendant complementary H-bonding groups.

The alkylated derivatives of aromatic acids, and self-assembled structures made from those compounds, can also be used in combination with coloring agents in a variety of ink and coating compositions, such as in liquid (aqueous or nonaqueous) printing ink vehicles, including inks used in conventional pens, markers and the like, liquid inkjet ink compositions, solid or phase change ink compositions, paints and automotive coatings, and the like. For example, the compounds can be formulated into a variety of ink vehicles, including solid and phase-change inks with melt temperatures of about 60 to about 130° C., solvent-based liquid inks or radiation-curable such as UV-curable liquid inks, and even aqueous inks.

In addition to ink compositions, the compounds can be used in combination with coloring agents in a variety of other applications, such as for paints, resins and plastics, lenses, optical filters, and the like according to applications thereof. By way of example only, the compounds can be used for toner compositions, which include polymer particles and pigment particles, along with other compounds that are formed into toner particles and optionally treated with internal or external additives such as flow aids, charge control agents, charge-enhancing agents, filler particles, radiation-curable agents or particles, surface release agents, and the like. Toner compositions can be prepared by a number of known methods including extrusion melt blending of the toner resin particles, pigment particles and other colorants and other optional additives, followed by mechanical comminution and classification. Other methods include those well known in the art such as spray drying, melt dispersion, extrusion processing, dispersion polymerization, and suspension polymerization. Further, the toner compositions can be prepared by emulsion/aggregation/coalescence processes, as disclosed in references U.S. Pat. Nos. 5,290,654, 5,278,020, 5,308,734, 5,370,963, 5,344,738, 5,403,693, 5,418,108, 5,364,729, 5,346,797, 7,547,499, 7,524,599, 7,442,740, 7,429,443, 7,425,398, 7,419,753, 7,402,371, 7,358,022, 7,335,453, and 7,312,011, the entire disclosures of which are incorporated herein by reference. The toner particles can in turn be mixed with carrier particles to form developer compositions. The toner and developer compositions can be used in a variety of electrophotographic printing systems.

Examples are set forth herein below and are illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

Synthesis of benzoic acid derivative (Table 1, compound 10 (m=11, n=9))

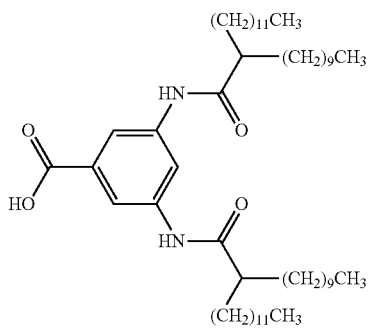

Step I: Synthesis of 2-decyltetradecanoyl chloride

2-Decyltetradecanoic acid (ISOCARB 24 from Sasol America, 1.15 g, 3.13 mmol) and dry tetrahydrofuran (20 mL) are mixed in a 100 mL vessel with stirring under an inert atmosphere. The mixture is cooled to 0° C. for at least 30 min, a catalytic amount of N,N'-dimethylformamide (4 drops) is added, followed by the slow, dropwise addition of oxalyl chloride (1 mL, 12.6 mmol). The reaction is then allowed to slowly warm to room temperature is allowed to stir for 30 min prior to removing the solvent by rotary evaporation. The acid chloride compound thus obtained was used in the next step without further purification.

Step II: Synthesis of methyl 3,5-bis(2'-decyltetradecanamido)benzoate

Methyl 3,5-diaminobenzoate (260.8 mg, 1.9 mmol) is dissolved in dry tetrahydrofuran (5 mL) in a 100 mL vessel under an inert atmosphere. Triethylamine (0.7 mL, 4.99 mmol) is then added and the solution is cooled to 0° C. A solution of 2-decyltetradecanoyl chloride from Step I in dry tetrahydrofuran (10 mL) is then added slowly, dropwise. The reaction is then allowed to slowly warm to room temperature. After stirring overnight, the reaction is quenched with water and the tetrahydrofuran is removed by rotary evaporation. The crude product residue is then dissolved in diethyl ether (50 mL) and is washed with deionized water (20 mL). The ether layer is separated and concentrated to give methyl 3,5-bis(2'-decyltetradecanamido)benzoate as a pale pink solid (1.17 g).

Step III—Saponification of methyl 3,5-bis(2'-decyltetradecanamido)benzoate

Methyl 3,5-bis(2'-decyltetradecanamido)benzoate from Step II, potassium hydroxide (0.38 g, 5.77 mmol), and methanol (20 mL) are added to a 50 mL vessel and heated to reflux. Deionized water (10 mL) is then added and the reaction is held at reflux overnight. The reaction is then cooled to room temperature, which results in the formation of an oil phase. Diethyl ether (20 mL) is added, and the aqueous phase is removed. The organic phase is then washed successively with 1 M hydrochloric acid (30 mL), 0.1 M hydrochloric acid (30 mL), and deionized water twice (30 mL each), before concentrating the ether layer by rotary evaporation, and drying in vacuo to give 3,5-bis(2'-decyltetradecanamido)benzoic acid as a light brown waxy solid (1.33 g, 99%). The product is identified by $^1$H and $^{13}$C NMR spectroscopy and ESI-MS and is of satisfactory purity.

Example 2

Synthesis of 5-(2-decyltetradecanamido)isophthalic acid (Table 1, compound 53)

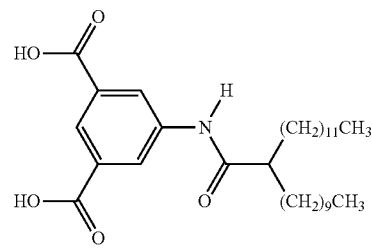

Step I—Synthesis of 2-decyltetradecanoyl chloride

2-Decyltetradecanoic acid (ISOCARB 24, obtained from Sasol America, TX, 7.65 g, 20.8 mmol) and dry tetrahydrofuran (100 mL) are added to a 500 mL single neck round bottom flask under an inert atmosphere. A catalytic amount of N,N'-dimethylformamide (0.28 mL, mmol) is then added, followed by the slow, dropwise addition of oxalyl chloride (7.3 mL, 83.7 mmol). The mixture is stirred for 10 min. until evolution of hydrochloric acid gas has ceased. The mixture is then stirred for an additional 3 h. before the solvent is removed by rotary evaporation to afford a viscous, pale yellow syrup. The acid chloride compound thus obtained was used in the next step without further purification.

Step II—Synthesis of 5-(2-decyltetradecanamido)isophthalic acid

Dimethyl 5-aminoisophthalate (Aldrich, 4.40 g, 21.0 mmol) is suspended in dry tetrahydrofuran (100 mL) in a 250 mL round bottom flask under an inert atmosphere. The dimethyl 5-aminoisophthalate suspension is cooled to 0° C. for at least 30 min., and an ice cold suspension of 2-decyltetradecanoyl chloride in of dry tetrahydrofuran (80 mL) is added slowly, dropwise. The reaction is then allowed to slowly warm to room temperature and stir overnight. Deionized water (10 mL) is added and the tetrahydrofuran is removed by rotary evaporation. The crude residue is then dissolved in 250 mL of ethyl acetate, and is washed with 3 successive 100 mL portions of deionized water. The ethyl acetate is then removed from the organic phase by rotary evaporation and the product is dried in vacuo to give crude dimethyl 5-(2'-decyltetradecanamido)isophthalate (12.56 g) as a pale yellow solid.

Step III—Saponification of Dimethyl 5-(2'-decyltetradecanamido)isophthalate

Dimethyl 5-(2'-decyltetradecanamido)isophthalate from Step II, potassium hydroxide (4.67 g, 0.0832 mol), and methanol (100 mL) are added to a 500 mL vessel and the mixture heated and maintained at reflux overnight. The reaction is then cooled to room temperature to give a turbid red-orange mixture. The mixture is then acidified with hydrochloric acid (7 mL) to give a white precipitate, which is collected by suction filtration, washed with deionized water, and then dried in vacuo to give an off-white powder (11.7 g). The product is identified by $^1$H and $^{13}$C NMR spectroscopy and ESI-MS and is of satisfactory purity.

Example 3

Synthesis of 5-(2-decyltetradecanamido)isophthalamide (Table 1, compound 74 (m=11, n=9))

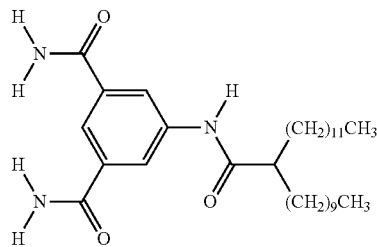

A 100 mL round bottom flask is charged with 0.50 g of 5-(2'-decyltetradecanamido)isophthalic acid (from Example 2, 0.89 mmol), which was dissolved in 20 mL of anhydrous tetrahydrofuran with stirring while under a nitrogen atmosphere. 0.3 mL of oxalyl chloride (3.55 mmol) and 2 drops of N,N'-dimethylformamide are added, and the reaction is allowed to stir for 2 h, before removing the tetrahydrofuran by rotary evaporation. The crude solution is resuspended in 5 mL of dry tetrahydrofuran while under nitrogen, and then is cooled to 0-5° C. using an ice-water bath. 4 mL of concentrated 30% ammonium hydroxide is then added and the reaction is allowed to slowly warm to room temperature and stir for 2 days. The solvent is removed by rotary evaporation. Then the crude solid is resuspended in 75 mL of chloroform and washed with 50 mL of deionized water. The chloroform is removed by rotary evaporation. 100 mL of ethyl acetate is added and the mixture was washed with 3 portions of deionized water (50 mL each). The ethyl acetate is then removed by rotary evaporation to give 0.44 g of isophthalamide compound 74 (Table 1, m=11, n=9) as a white solid (94%). The $^1$H and $^{13}$C NMR spectra are consistent with the structure of compound 74 (Table 1, m=11, n=9) in satisfactory purity.

Example 4

Synthesis of Bis Isophthalic Acid Compound 1 (Table 3)

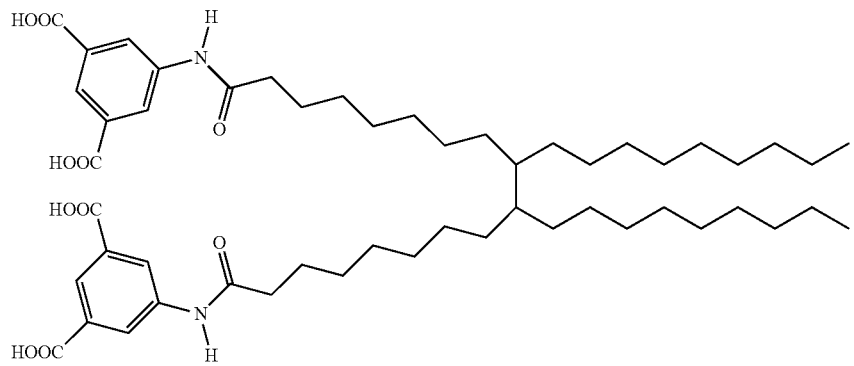 [SMILES: CCCCCCCCCC(CCCCCCCC(=O)Nc1cc(C(=O)O)cc(C(=O)O)c1)C(CCCCCCCCC)CCCCCCCC(=O)Nc1cc(C(=O)O)cc(C(=O)O)c1]

Step I—Synthesis of Bis Isophthaloyl Tetrachloride

Pripol®1006 (96%, Uniqema, 3.23 g, 5.70 mmol) and dry tetrahydrofuran (50 mL) are added to a 250 mL round bottom flask under an inert atmosphere. The solution is then cooled to 0° C. for at least 30 min. before a catalytic amount of N,N'-dimethylformamide (0.10 mL, 1.3 mmol) is added, followed by the slow, dropwise addition of oxalyl chloride (2.0 mL, 23.3 mmol). The mixture is then slowly allowed to warm to room temperature and is stirred for 3.5 h. before the solvent is removed by rotary evaporation to afford a colorless liquid with solid suspended white solid. The tetraacid chloride compound thus obtained was used in the next step without further purification.

Step II—Synthesis of Tetraester Intermediate

The tetraacid chloride from Step I and dry tetrahydrofuran (50 mL), were mixed under an inert atmosphere and the mixture was cooled to 0° C. for at least 30 min. Dimethyl 5-aminoisophthalate (Aldrich, 2.65 g, 12.7 mmol) is then added as a solution in dry N,N-dimethylformamide (15 mL) in slowly, dropwise to the flask containing the tetraacid chloride chloride. Two successive rinses with tetrahydrofuran (10 mL) were done to quantitatively transfer all of the amine to the acid chloride flask. Triethylamine (2.6 mL, 18.7 mmol) was then added and the reaction is then allowed to slowly warm to room temperature and stir overnight. After removing the tetrahydrofuran by rotary evaporation, the crude residue is then dissolved in 140 mL of diethyl ether, and is washed with deionized water (40 mL), saturated sodium bicarbonate (40 mL), 5% citric acid (40 L), and brine (40 mL). The diethyl ether layer is then dried over sodium sulfate, filtered through glass wool, the solvent removed by rotary evaporation, and dried in vacuo to give crude tetramethyl bis isophthalate (5.61 g) as a viscous, yellow syrup. The diester thus obtained is used in the next step without further purification.

Step III—Saponification of the Tetramethyl Bis Isophthalate Intermediate

The tetraester from Step II, potassium hydroxide (15.38 g, 233 mmol), methanol (200 mL), and deionized water (100 mL) are added to a 500 mL vessel and the mixture was heated to reflux for 1 h. The reaction is then cooled to room temperature and acidified with 5M hydrochloric acid (50 mL) to give a white precipitate, which is collected by suction filtration, washed with deionized water, and then dried in vacuo to give a pale orange-yellow powder (4.62 g, 91%). The product is identified by $^1$H and $^{13}$C NMR spectroscopy and ESI-MS and is of satisfactory purity.

Example 5

Synthesis of 5-(butyramido)isophthalic acid compound 45 (m=3, Table 1)

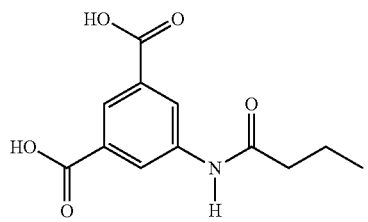 [SMILES: CCCC(=O)Nc1cc(C(=O)O)cc(C(=O)O)c1]

Step I—Synthesis of dimethyl 5-(butyramido)isophthalate

Dimethyl 5-aminoisophthalate (Aldrich, 0.7685 g, 3.67 mmol) is suspended in dry tetrahydrofuran (20 mL) in a 250 mL round bottom flask under an inert atmosphere. Methyl amine (1.00 mL, 7.17 mmol) is added and the suspension is cooled to 0° C. for at least 30 min., before an ice cold suspension of butyryl chloride is added slowly, dropwise. The reaction is then allowed to slowly warm to room temperature and stir overnight. Deionized water (20 mL) and diethyl ether (50 mL) are then added. The aqueous layer is removed and the organic layer is washed with saturated sodium bicarbonate (10 mL), deionized water (10 mL), 5% citric acid (10 mL), deionized water (10 mL), and then brine (10 mL). After separating the organic layer is dried over sodium sulfate, filtered through glass wool, and then the ether is removed by rotary evaporation to give crude dimethyl 5-(butyramido) isophthalic acid diester (1.02 g) as a white solid. The diester thus obtained was used in the next step without further purification.

Step II—Saponification of dimethyl 5-(butyramido)isophthalate

Dimethyl 5-(butyramido)isophthalic acid diester from Step I, potassium hydroxide (2.06 g, 35.6 mmol) and methanol (30 mL) are added to a 50 mL vessel and the mixture heated to reflux for 1 h. The reaction is then cooled to room temperature and is acidified with 5M hydrochloric acid to give a white precipitate, which is collected by suction filtration, washed with deionized water, and then dried in vacuo to give an off-white powder (0.770 g, 75%). The product is identified by $^1$H and $^{13}$C NMR spectroscopy and ESI-MS and is of satisfactory purity.

Example 6

Synthesis of Octadecyl Ureido Compound 56 (Table 1)

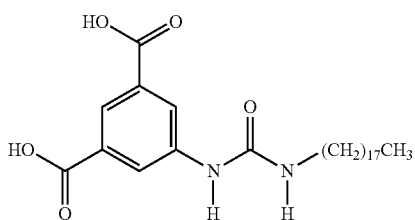

Step I—Synthesis of dimethyl 5-(octadecylureido)isophthalate

Dimethyl 5-aminoisophthalate (Aldrich, 0.441 g, 2.12 mmol) is dissolved in dry N,N-dimethylformamide (8 mL) in a 50 mL round bottom flask under an inert atmosphere. A 2.12 M solution of octadecylisocyanate (2.12 mmol) in dry N,N-dimethylformamide (1 mL) is then added dropwise. The residual octadecylisocyanate solution is quantitatively transferred with 2 portions of N,N'-dimethylformamide (1 mL each) and the reaction is stirred overnight at room temperature. The reaction is then heated to 100° C. for 22 h, and then cooled to room temperature to give a white slurry. The solid is then vacuum filtered, washed with fresh N,N-dimethylformamide followed by deionized water. The filtrate is then concentrated by rotary evaporation to give a white solid.

Step II—Saponification of dimethyl 5-(octadecylureido)isophthalate

Crude dimethyl 5-(octadecylureido)isophthalate Step I (330 mg, 0.654 mmol) is suspended in methanol (15 mL). Potassium hydroxide (0.1983 mg, 3.53 mmol) is then added and the mixture is heated to reflux for 2 h. After cooling to room temperature, the suspended white solid is recovered by filtration, and washed with cold methanol. The crude solid is then suspended in 1 M hydrochloric acid and stirred for 2 days, after which the product is collected by filtration, washed with deionized water, and dried in vacuo to yield a white powder (124.8 mg). The product is identified by $^1$H and $^{13}$C NMR spectroscopy and ESI-MS and is of satisfactory purity.

Example 7

Synthesis of 5-(hexadecyloxy)isophthalic acid compound 61 (Table 1)

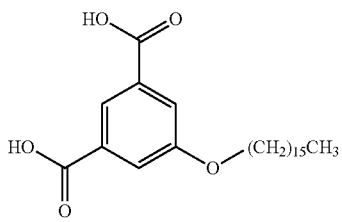

Step I—Synthesis of dimethyl 5-(hexadecyloxy)isophthalate

A 100 mL round bottom flask is charged with dimethyl-5-hydroxyisophthalic acid (0.2584 g, 1.23 mmol), potassium carbonate (0.356 g, 2.58 mmol), and potassium iodide (0.2018 g, 1.22 mmol) under an inert atmosphere. Anhydrous N,N'-dimethylformamide (10 mL) is added and the mixture is heated to 60° C. for 2 h. Bromohexadecane (0.376 mL, 1.23 mmol) is then added and the reaction is stirred overnight. After cooling to room temperature the reaction is concentrated by rotary evaporation. The crude solid is suspended in diethyl ether (40 mL), and is successively washed with deionized water (20 mL), citric acid (5 wt %, 20 mL), deionized water (20 mL), and brine (20 mL). The ether layer is separated, filtered through glass wool, concentrated by rotary evaporation, and dried in vacuo to yield and off-white solid (0.53 g, 100%).

Step II—Saponification of dimethyl 5-(hexadecyloxy)isophthalate

A 50 mL vessel was charged with dimethyl 5-(hexadecyloxy)isophthalate from Step I (0.44 g, 1.01 mmol) and methanol (20 mL) and heated to reflux. Potassium hydroxide (0.388 g, 5.88 mmol) was then added in portions over a period of 8.5 h. The reaction is then cooled to room temperature and acidified with 5 M hydrochloric acid (7 mL). Deionized water (20 mL) is then added and the precipitate is collected by suction filtration, and is washed with deionized water, and dried in vacuo to give a white powder (0.3671 g, 73% yield). The product is identified by $^1$H and $^{13}$C NMR spectroscopy and ESI-MS and is of satisfactory purity.

Example 8

Gel Formation of Alkylated Derivatives of Aromatic Acids

The example demonstrates that the alkylated derivatives of aromatic acids of the present invention form the supramolecular assemblies (organogels) through hydrogen bonding and π-π interactions in appropriate organic solvents.
Gelation Test To vials with a screw cap lids (4 mL capacity) were added alkylated derivatives of aromatic acids as solids (1-100 mg) and a solvent (1 mL). The mixture was then sonicated and heated until clear solutions were obtained. After cooling and standing at room temperature for at least 30 min., the sample was inverted and inspected visually. If the sample did not flow or fall, it was judged to be a gel. Table 4 shows the gelator ability of the alkylated derivatives of aromatic acids described in Examples 1 to 7.

TABLE 4

| Compound/Solvent | 53[1] (m = 11, n = 9) | 56[1] (, m = 11, n = 9) | 10[1] (m = 11, n = 9) | 45[1] (m = 3) | 74[1] (m = 17) | 1[3] |
|---|---|---|---|---|---|---|
| H$_2$O | I (0.1) | I (0.1) | I (0.1) | I (0.1) | I (0.1) | I (0.2) |
| Ethylene Glycol | PG (2.0) | P (0.5) | I (4.0) | S (0.1) | P (2.5) | CG (2.0) |
| MeOH | S (0.1) | G (2.0) | P (2.0) | S | S (3.0) | S (10.0) |
| CHCl$_3$ | G (0.4) | I (0.1) | P (2.0) | I (0.1) | P (0.1) | I (0.2) |
| Cyclohexane | G (1.0) | — | CG (10) | — | I (0.1) | I (0.1) |
| Decalin | G (0.5) | G (2.3) | — | — | I (2.0) | I (1.0) |
| Benzene | G (0.4) | — | — | — | — | — |
| Toluene | G (1.0) | I (0.1) | VS (10) | I (1.3) | I (0.5) | I (0.1) |
| Xylenes | G (1) | G (2.0) | S (1.0) | — | I (2.0) | I (1.2) |
| Hexanes | P (0.2), | — | CG (5.0) | I (0.1) | I (0.1) | I |
| Dodecane | G (1) | — | — | — | — | — |
| Hexadecane | G (1) | I (0.1) | — | I (1.1) | — | I (1.3) |
| Dimethoxyethane | G (0.6) | S (1.0) | — | — | S (0.1) | S (2.0) |

[1]Table 1.
[3]Table 3.
Values in parentheses are concentration in wt %
I = insoluble
P = precipitate
S = solution
VS = viscous solution
G = gel
PG = partial gel

Example 8

Self-Assembled Nanostructures from Alkylated Derivatives of Aromatic Acids by Electron Microscopy This example describes the self-assembled nanostructures formed from alkylated derivatives of aromatic acids deposited onto substrates observed by Scanning Electron and Scanning Transmission Electron Microscopy (SEM and STEM, respectively).

Figure 2A:
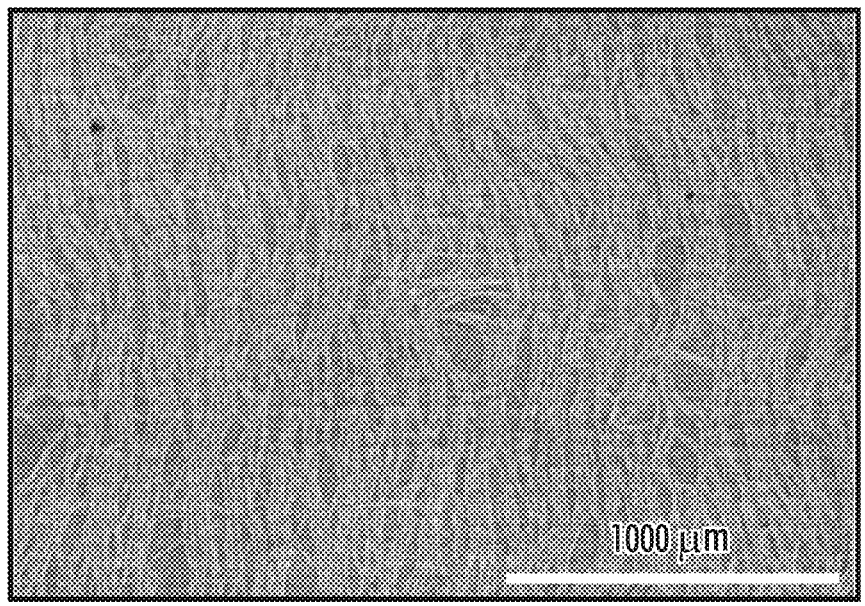
FIGS. 2A and 2B show SEM images of a material of Example 2.
Figure 2B:
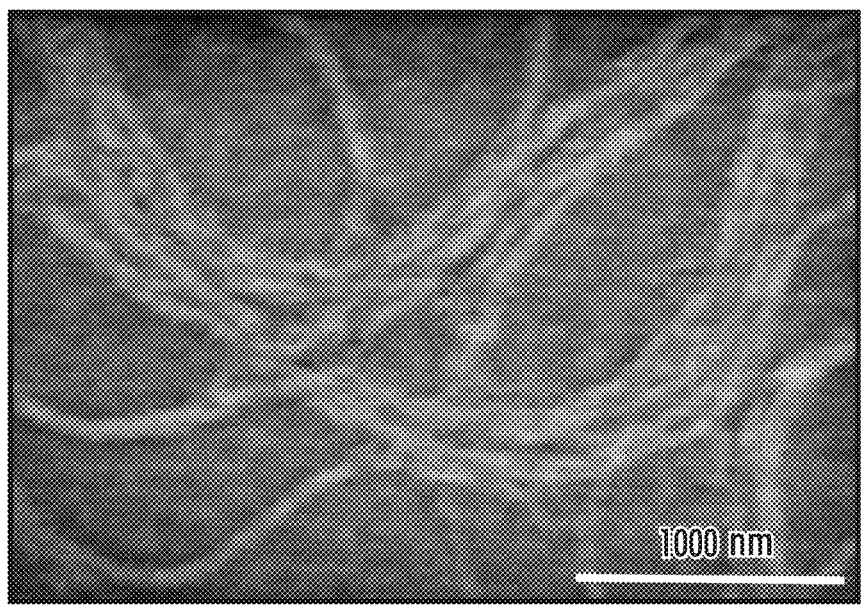
Figure 3A:
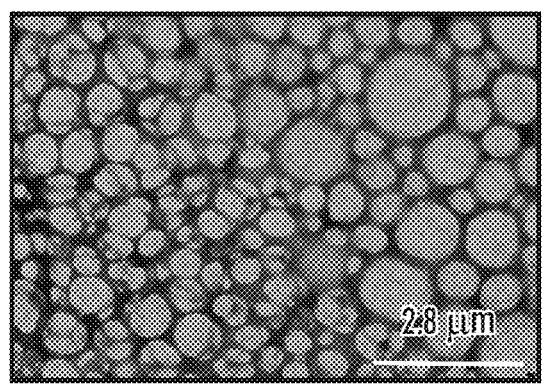
FIGS. 3A, 3B, and 3C show SEM images of a material of Example 3.
Figure 3B:
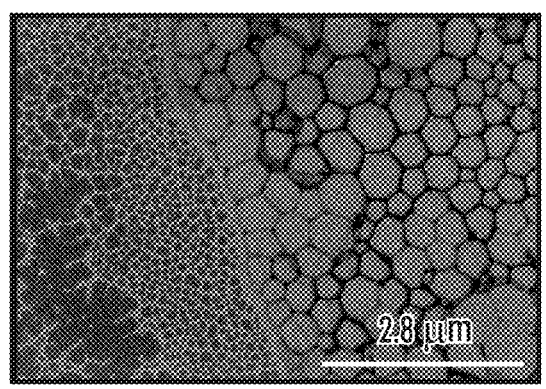
Figure 3C:
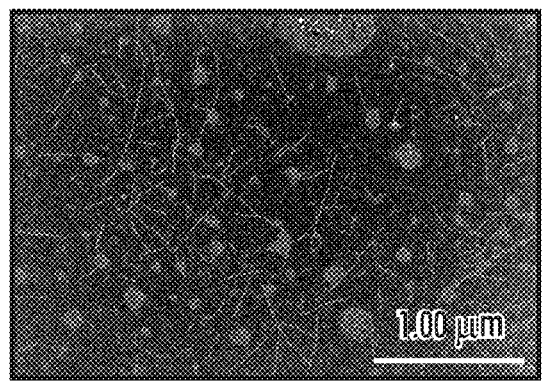
Figure 4A:
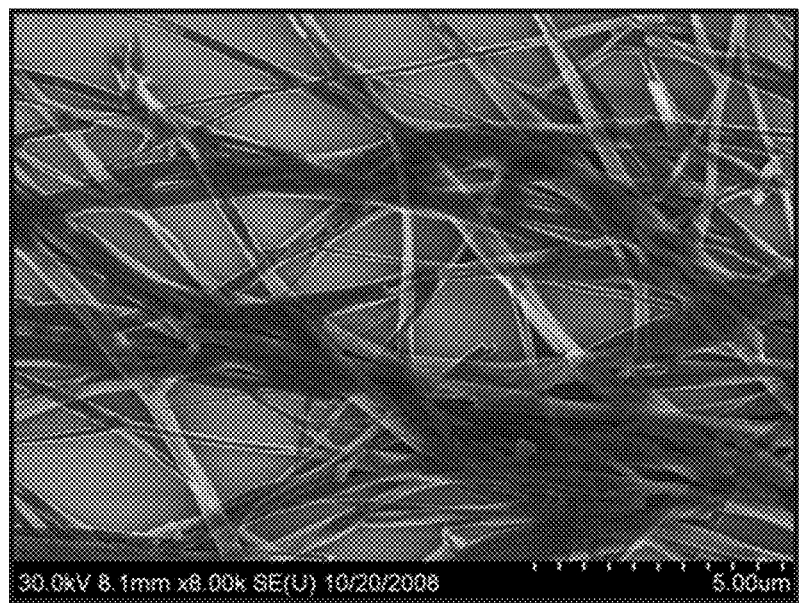
FIGS. 4A and 4B show SEM images of a material of Example 3.
Figure 4B:
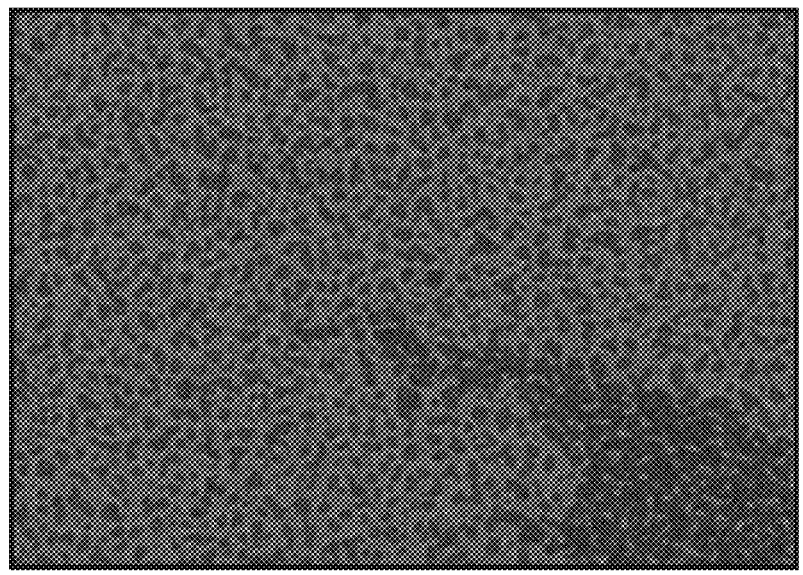
Figure 5:
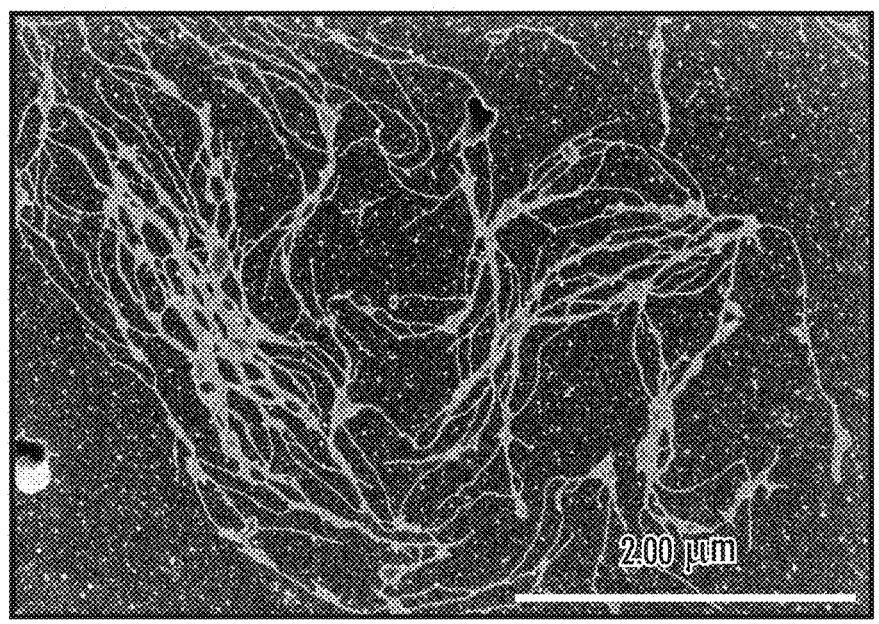
FIG. 5 shows SEM images of a material of Example 4.
Figure 6A:
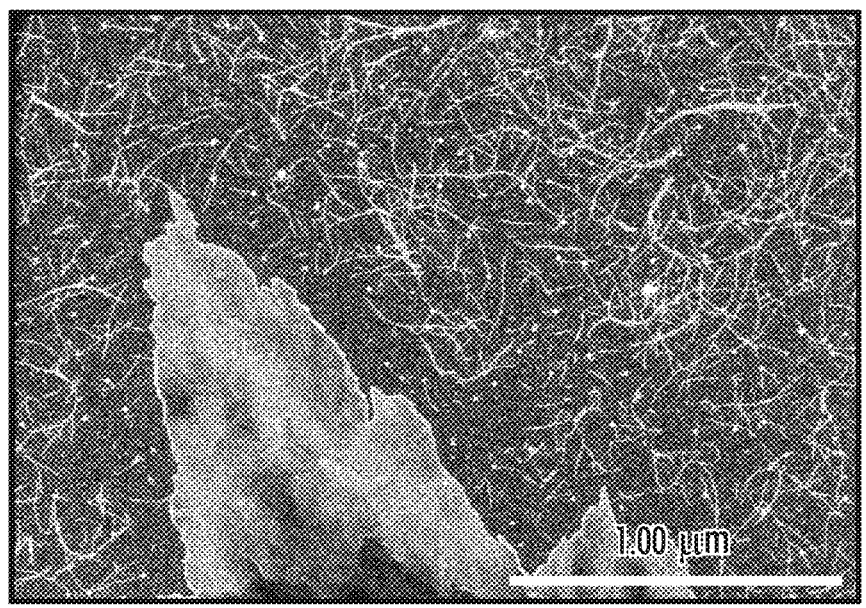
FIGS. 6A and 6B show SEM images of a material of Example 5.
Figure 6B:
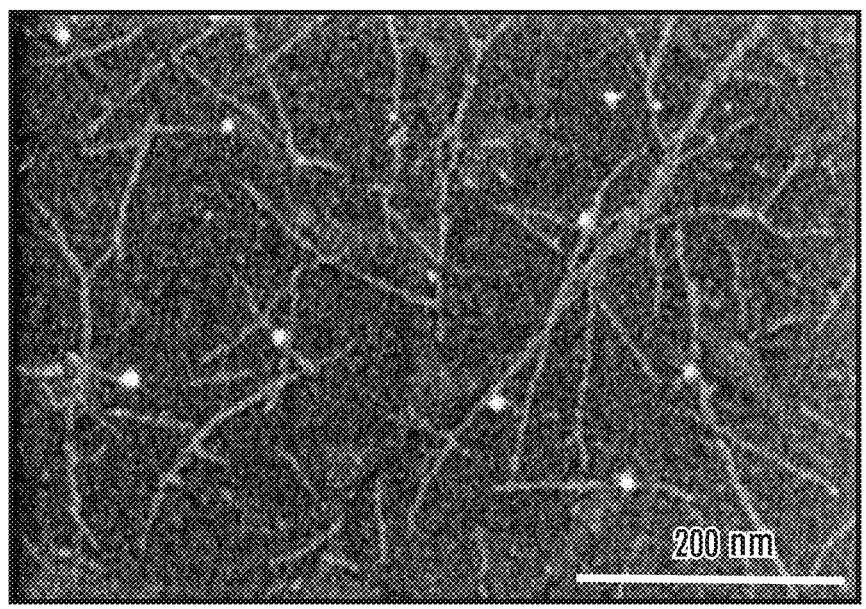
Figure 7A:
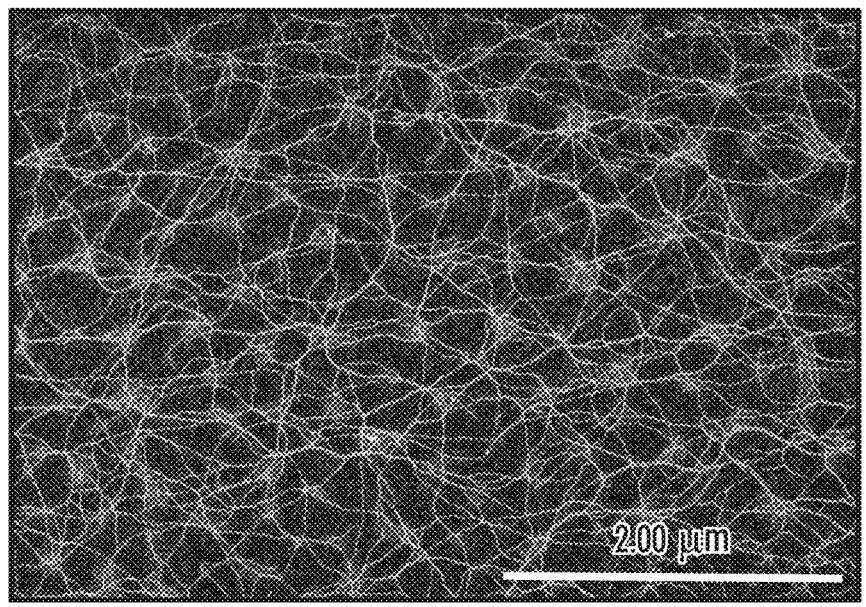
FIGS. 7A and 7B show SEM images of a material of Example 6.
Figure 7B:
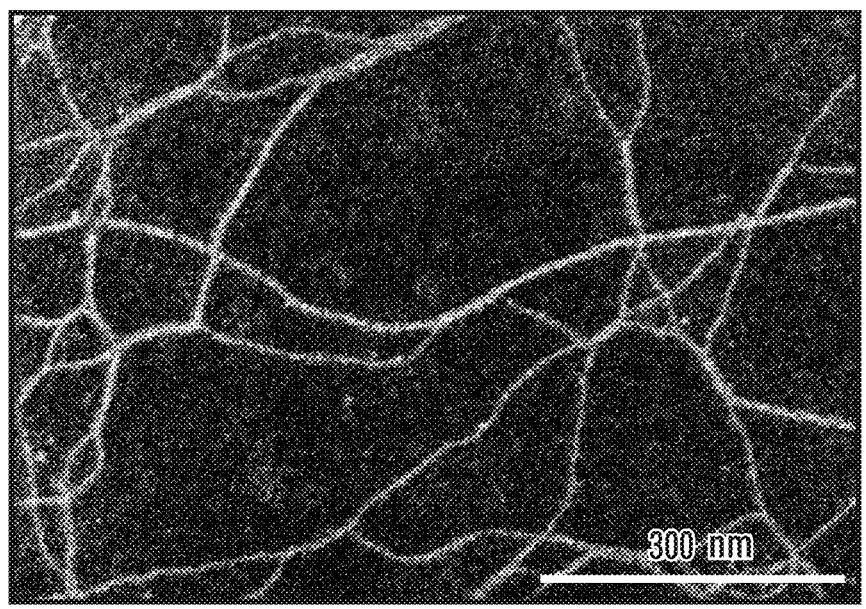

Microscopy samples are prepared by mixing the alkylated derivatives of aromatic acids as solids with a solvent, subjecting the mixture to bath sonication, and then heating to form a clear solution. The solutions are then cooled to room temperature and allowed to age for desired periods of time prior to microscopy sample preparation. After cooling, the samples may be clear solutions, turbid colloidal solutions, or more opaque dispersions. Microscopy samples are prepared for analysis by depositing a drop on thin carbon film coated copper mesh grids, allowing the drop to remain on the film for a desired period of time, followed by wicking away the excess solvent with filter paper and allowing to dry. Table 5 summarizes examples of compositions containing nanostructures of alkylated derivatives of selected aromatic acids for this invention. FIGS. 1 to 7 show Scanning Electron Microscopy and Scanning Transmission Electron Microscopy images of the nanostructures formed from alkylated derivatives of selected aromatic acids.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A nanostructure comprising molecules non-covalently bound to each other of at least one compound selected from the group consisting of the following compounds:

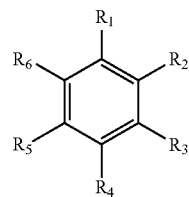

$R_4$ and $R_6$ = H

| $R_1$ | $R_2$ | $R_3$ |
|---|---|---|
| —COOH | H | —COOH |
| —COOH | H | —COOH |
| H | —COOH | 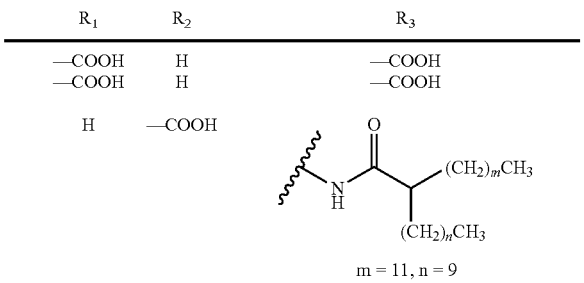 |

$m = 11, n = 9$
$m = 7, n = 5$
$m = 5, n = 3$

TABLE 5

| Compound | Solvent | Conc. (mg/mL) | Description | W (nm) | L (nm) |
|---|---|---|---|---|---|
| 53 (m = 11, n = 9)[1] | Toluene | 0.1 | Bundles of fibrils | 20-100 | >1000 |
|  |  |  | Fibrils | 5-10 | >1000 |
| 56 (m = 11, n = 9)[1] | Chloroform | 0.1 | Fibrils | 5-10 | >1000 |
| 10 (m = 11, n = 9)[1] | Cyclohexane | 1.0 | Fibrils | 15-55 | 200-1000 |
| 45 (m = 3)[1] | Xylenes:THF (1:1) | 1.3 | Sheets | — | 2000-10000 |
|  |  |  | Fibrils | 3-6 | 50-1000 |
| 74 (m = 11, n = 9)[1] | Chloroform | 1.0 | Fibers | 25-200 | 300-800 |
|  |  | 0.1 | Fibrils | 5-10 | 50-1000 |
|  | EtOH:H$_2$O | 1.0 | Fibers | 50-250 | >5000 |
|  |  |  | Fibrils | 5-10 | 10-100 |
| 1[3] | Xylenes | 0.4 | Fibrils | 5-10 | 200-2000 |

[1]Table 1,
[3]Table 3,
THF = tetrahydrofuran

-continued

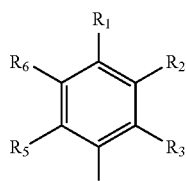

$R_4$ and $R_6$ = H

| H | —COOH | 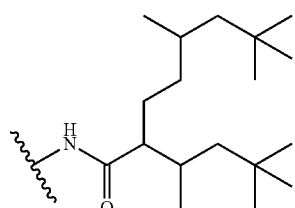 |
|---|---|---|

$R_5$

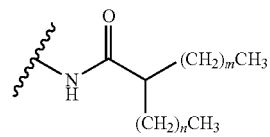

m = 11, n = 9

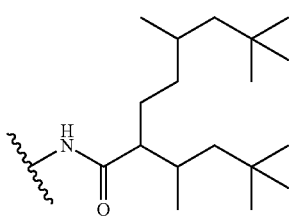

—COOH
—COOH and mixtures thereof.

2. A marking material composition comprising the nanostructure of claim 1.

3. The marking material of claim 2, wherein the marking material is an ink, a toner, a developer, a paint, or a coating.

4. An organogel composition comprising the nanostructure of claim 1.

5. The nanostructure of claim 1, wherein the compound is amphiphilic, comprising at least one hydrophilic or polar functional group with available heteroatoms for hydrogen-bonding with other molecules of the compound, and at least one non-polar or hydrophobic sterically bulky group.

6. The nanostructure of claim 1, wherein the non-covalent bonding is predominately through hydrogen-bonding, aromatic pi-pi interactions, and van der Waals' forces.

7. The nanostructure of claim 1, wherein the nanostructure is formed by homogeneously mixing the compound with a polar or nonpolar liquid under conditions to effect dissolution and self-assembly of the compound.

8. The nanostructure of claim 1, comprising at least two different alkylated derivatives of aromatic acids.

9. The nanostructure of claim 1, wherein the nanostructure is a one-dimensional structure in the form of a nanofibril or nanofiber.

10. The nanostructure of claim 1, wherein the nanostructure is a two-dimensional structure.

11. The nanostructure of claim 1, wherein the nanostructure is a three-dimensional structure in the form of a non-covalent gelator network or gel.

12. The nanostructure of claim 1, wherein the nanostructure has, in at least one dimension, a size ranging from about 1 to about 500 nm, and has a largest dimension of up to about 5000 nm.

* * * * *